(12) United States Patent
Denda

(10) Patent No.: US 11,495,715 B2
(45) Date of Patent: Nov. 8, 2022

(54) ELECTRONIC DEVICE

(71) Applicant: SHINKO ELECTRIC INDUSTRIES CO., LTD., Nagano (JP)

(72) Inventor: Tatsuaki Denda, Nagano (JP)

(73) Assignee: SHINKO ELECTRIC INDUSTRIES CO., LTD., Nagano (JP)

(*) Notice: Subject to any disclaimer, the term of this patent is extended or adjusted under 35 U.S.C. 154(b) by 184 days.

(21) Appl. No.: 17/094,668

(22) Filed: Nov. 10, 2020

(65) Prior Publication Data
US 2021/0151634 A1 May 20, 2021

(30) Foreign Application Priority Data

Nov. 14, 2019 (JP) ............................. JP2019-206308

(51) Int. Cl.
H01L 33/48 (2010.01)
H01L 33/62 (2010.01)
H01L 31/02 (2006.01)
H01L 31/173 (2006.01)
A61B 5/145 (2006.01)
A61B 5/00 (2006.01)
A61B 5/1455 (2006.01)
H01L 25/16 (2006.01)

(52) U.S. Cl.
CPC ............ H01L 33/486 (2013.01); H01L 33/62 (2013.01); *H01L 31/02013* (2013.01)

(58) Field of Classification Search
CPC ..... H01L 33/48; H01L 33/62; A61B 5/14532; A61B 5/0002; A61B 5/14551
See application file for complete search history.

(56) References Cited

U.S. PATENT DOCUMENTS

| 2006/0155183 | A1  | 7/2006 | Kroecker et al. |
| 2007/0038048 | A1* | 2/2007 | Gerder ................ A61B 5/6838 600/323 |
| 2011/0237922 | A1  | 9/2011 | Parker, III et al. |
| 2011/0237924 | A1  | 9/2011 | McGusty et al. |

FOREIGN PATENT DOCUMENTS

JP 2004529709 A 9/2004

* cited by examiner

*Primary Examiner* — Marcos D. Pizarro
*Assistant Examiner* — Antonio B Crite
(74) *Attorney, Agent, or Firm* — Tarolli, Sundheim, Covell & Tummino LLP

(57) ABSTRACT

An electronic device includes: a support body including first and second planar portions facing each other, a first connecting portion connecting the first and second planar portions, and a first receptacle surrounded by the first and second planar portions and the first connecting portion; a projection being part of the second planar portion projecting outward from the first receptacle outside the first planar portion in plan view; a wiring substrate including a facing surface facing the support body and an opposite surface opposite to the facing surface, the wiring substrate being folded and attached along an inner surface of the first receptacle and a surface of the projection continuous with the inner surface of the first receptacle; a sensor element mounted on the facing surface attached to the inner surface of the first receptacle; and an antenna mounted on the opposite surface attached to the surface of the projection.

10 Claims, 14 Drawing Sheets

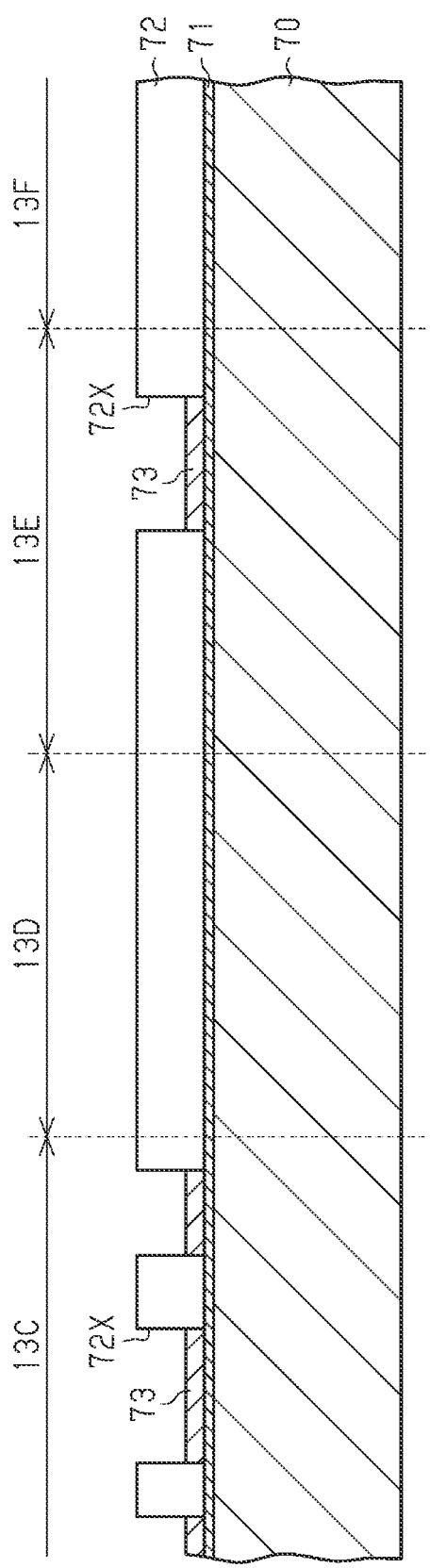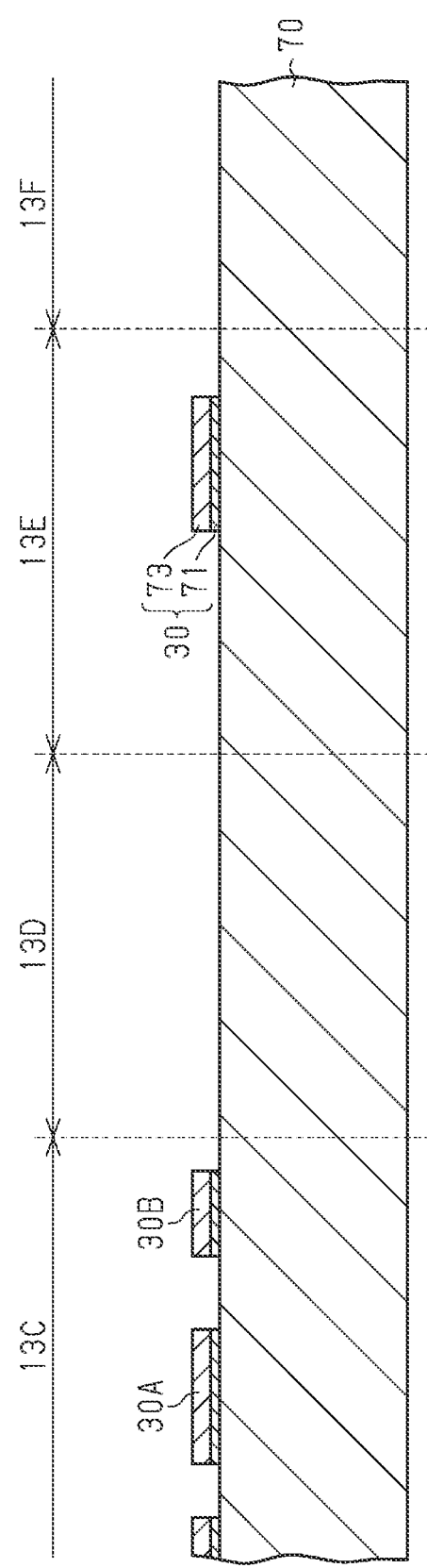

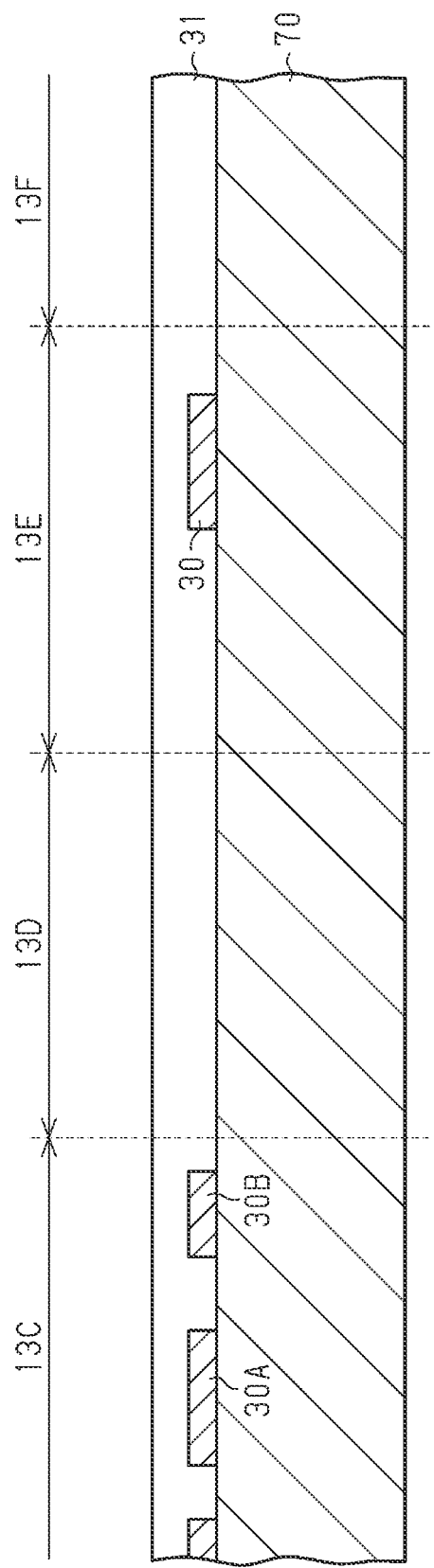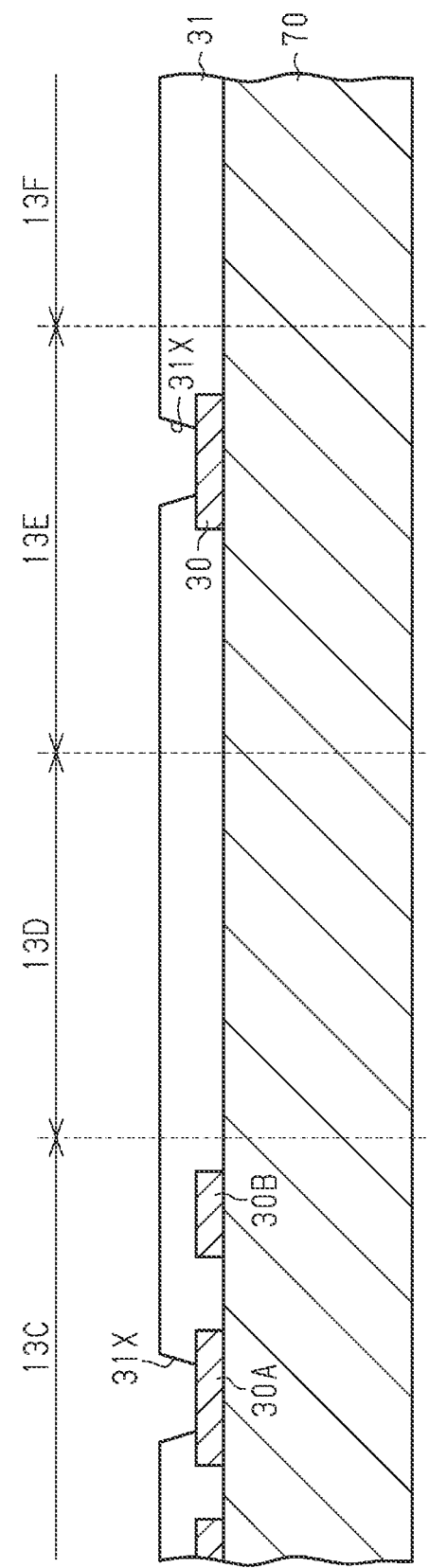

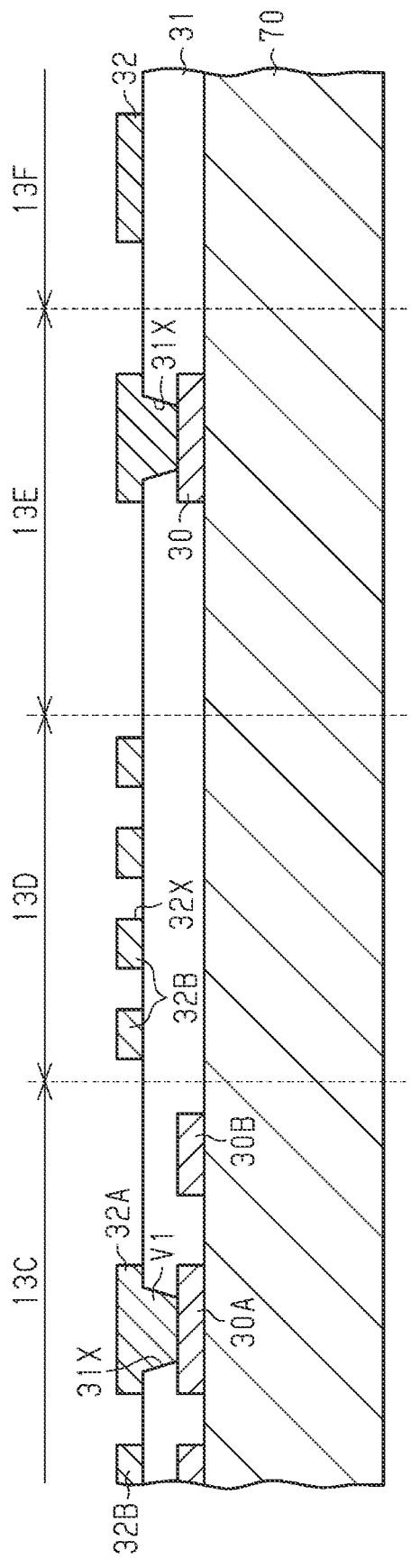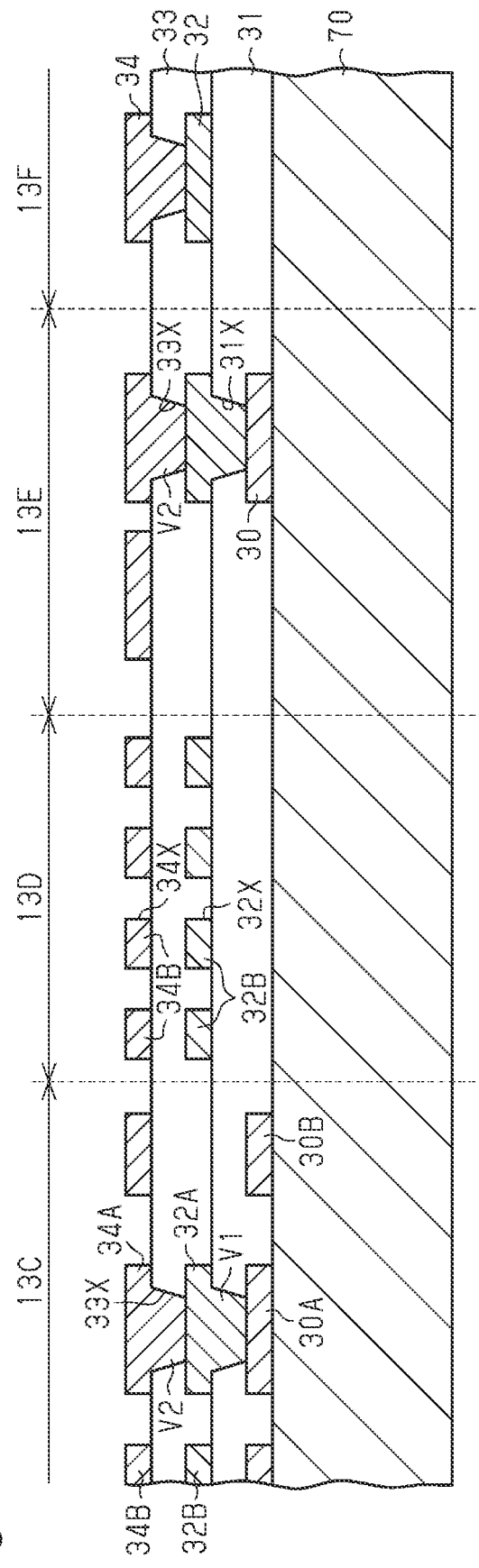

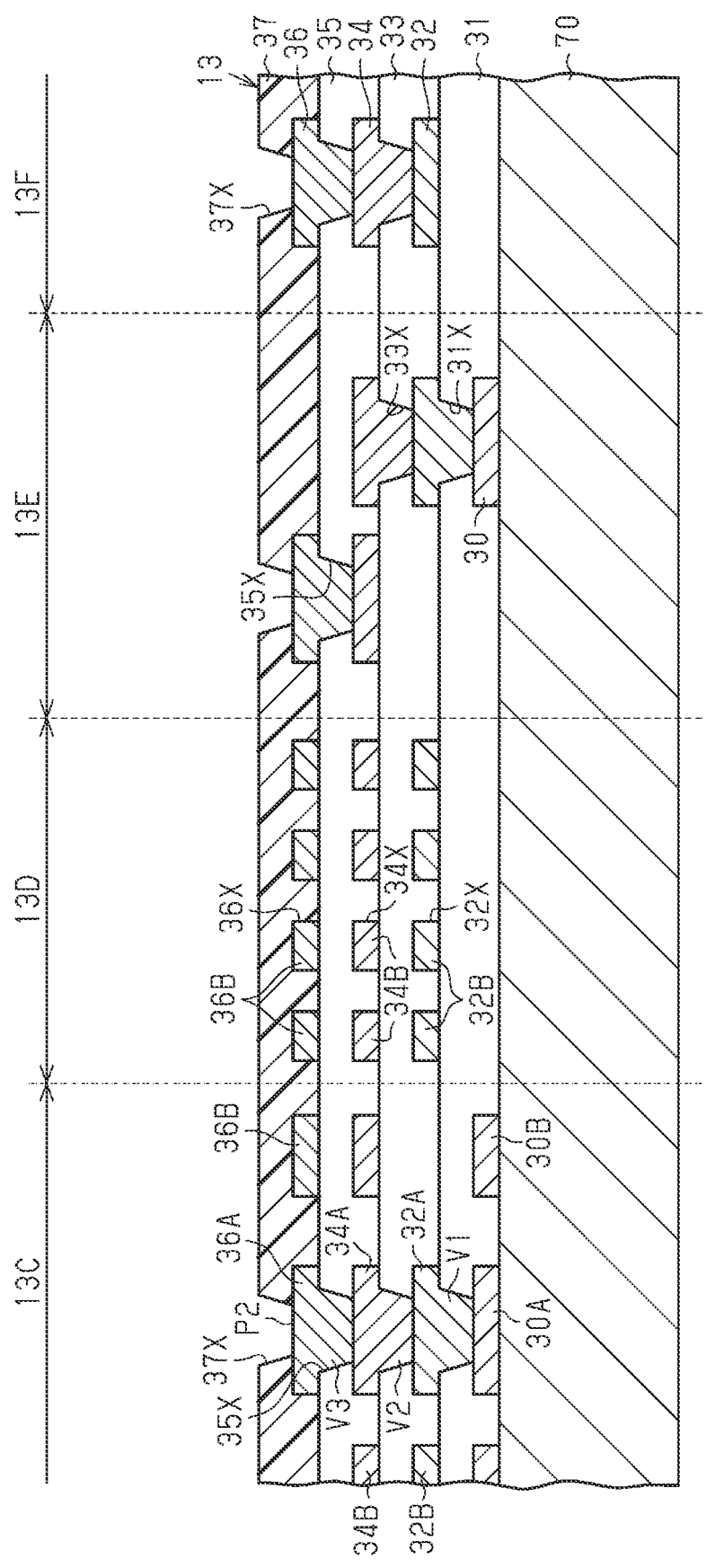

Bending Direction

Bending Direction

ELECTRONIC DEVICE

CROSS-REFERENCE TO RELATED APPLICATIONS

This application is based upon and claims the benefit of priority from prior Japanese Patent Application No. 2019-206308, filed on Nov. 14, 2019, the entire contents of which are incorporated herein by reference.

FIELD

The present disclosure relates to an electronic device.

BACKGROUND

Japanese National Phase Laid-Open Patent Publication No. 2004-529709 discloses a typical electronic device that is a biometric information measurement device (sensor device) configured to be attached to the body of an examinee and transmit a signal corresponding to biometric information of the examinee through wireless communication. This type of electronic device includes a sensor unit that detects an electric signal corresponding to the biometric information of the examinee. The electric signal detected by the sensor unit undergoes a given signal process and then is transmitted to an external device from an antenna through wireless communication.

SUMMARY

The properties of the antenna are readily adversely affected by other electronic components and the body of the examinee. In this point, there is still room for improvement.

An embodiment of an electronic device includes a support body, a projection, a wiring substrate, a sensor element, and an antenna. The support body includes a first planar portion and a second planar portion that are arranged facing each other, a first connecting portion connecting a first end of the first planar portion to a first end of the second planar portion, and a first receptacle surrounded by the first planar portion, the first connecting portion, and the second planar portion. The projection projects outward from the first receptacle and is located outside the first planar portion in plan view. The projection is part of the second planar portion. The wiring substrate includes a facing surface facing the support body and an opposite surface so that the opposite surface and the facing surface are located at opposite sides of the wiring substrate. The wiring substrate is folded and attached along an inner surface of the first receptacle and also attached along a first surface of the projection that is continuous with the inner surface of the first receptacle. The sensor element is mounted on the facing surface of the wiring substrate at a portion of the wiring substrate attached to the inner surface of the first receptacle. The antenna is mounted on the opposite surface of the wiring substrate at a portion of the wiring substrate attached to the first surface of the projection.

BRIEF DESCRIPTION OF THE DRAWINGS

The embodiments, together with objects and advantages thereof, may best be understood by reference to the following description of the presently preferred embodiments together with the accompanying drawings in which:

FIGS. 7A, 7B, 8A, 8B, 9A, 9B, 10A, 10B, 11, and 12 are schematic cross-sectional views illustrating a method for manufacturing an embodiment of a semiconductor device;

DESCRIPTION OF THE EMBODIMENTS

Figure 1:
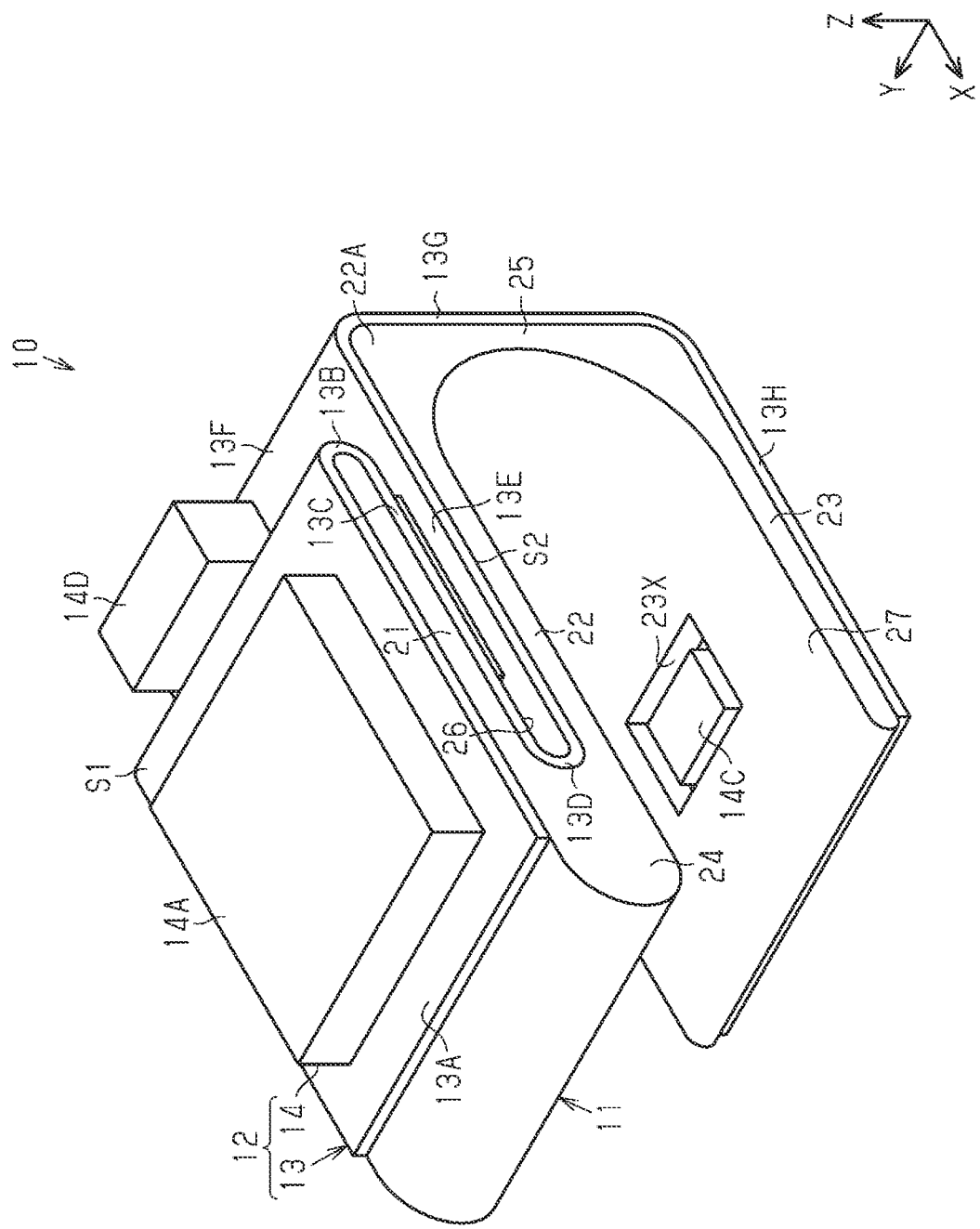
FIG. 1 is a schematic perspective view illustrating an embodiment of an electronic device.

An embodiment will be described below with reference to the accompanying drawings.

Elements in the drawings may be partially enlarged for simplicity and clarity and thus have not necessarily been drawn to scale. To facilitate understanding, hatching lines may not be illustrated or be replaced by shadings in the cross-sectional drawings. The terms "parallel," "orthogonal," and "horizontal" in this specification are not limited to exactly parallel, orthogonal, and horizontal, and includes generally parallel, orthogonal, and horizontal within the scope in which the operation and advantages of the embodiment are obtained.

Structure of Electronic Device 10

As illustrated in FIG. 1, an electronic device 10 includes, for example, a support body 11 and a semiconductor device 12 attached to the support body 11. The semiconductor device 12 includes, for example, a wiring substrate 13 attached to the support body 11 and electronic components 14 mounted on the wiring substrate 13. The electronic device 10 is, for example, a biometric information measurement device (sensor device) configured to be attached to the body of an examinee and obtain biometric information of the examinee. The electronic device 10 is configured to transmit the obtained biometric information through wireless communication. The biometric information includes, for example, a bioelectric potential, a body temperature, a blood oxygen saturation level, a pulse rate, and a blood sugar level. The bioelectric potential may be any bioelectric potential that captures changes in potential of the biometric information and includes, for example, an electrocardiogram, impedance respiration, thermistor respiration, heart rate, and cardiac output. The electronic device 10 of the present embodiment is configured to measure the blood oxygen saturation level of the examinee.

In the drawings, the x-axis indicates a front-rear direction of the electronic device 10, the y-axis indicates a width-wise direction of the electronic device 10 that is orthogonal to the x-axis, and the z-axis indicates a height-wise direction of the electronic device 10 that is orthogonal to an x, y-plane. In the description hereafter, for the sake of convenience, a direction extending along the x-axis is referred to as a front-rear direction X, a direction extending along the y-axis is referred to as a width-wise direction Y, and a direction extending along the z-axis is referred to as a height-wise direction Z. In addition, in the description hereafter, the direction indicated by arrow X and the direction indicated by arrow Z in FIG. 1 define frontward and upward, respectively. In this specification, "plan view" refers to a view of an object taken in the height-wise direction Z, and "planar shape" refers to a shape of an object taken in the height-wise direction Z.

Structure of Support Body 11

The support body 11 will now be described.

The support body 11 is, for example, set to have higher mechanical strengths (e.g., rigidity and hardness) than the wiring substrate 13. The support body 11 is, for example, used to support the wiring substrate 13. The support body 11 is, for example, elastic. The material of the support body 11 may be, for example, a material having a known electric permittivity. The material of the support body 11 may be, for example, a dielectric material having an electric permittivity of approximately 1 to 5. The material of the support body 11 may be, for example, an acrylic resin, polycarbonate, or an acrylonitrile butadiene styrene (ABS) resin. The support body 11 has, for example, a light blocking property. The material of the support body 11 may be, for example, a resin material dyed black or the like.

The support body 11 is, for example, S-shaped. The support body 11 has, for example, an S-shaped cross section. The support body 11 has, for example, an S-shaped side surface as viewed in the width-wise direction Y.

The support body 11 includes, for example, three planar portions 21, 22, and 23 facing each other, a connecting portion 24 connecting an end of the planar portion 21 to an end of the planar portion 22, and a connecting portion 25 connecting an end of the planar portion 22 to an end of the planar portion 23. The support body 11 is, for example, a single-piece component in which the planar portions 21, 22, and 23 and the connecting portions 24 and 25 are formed integrally with each other.

In this specification, the term "facing" refers to a state in which surfaces or members are located in front of each other. The term is not limited to a state in which surfaces or members are located completely in front of each other and includes a state in which surfaces or members are located partially in front of each other. Further, in this specification, the term "facing" includes both a state in which two parts are located with another member located between the two parts and a state in which another member is not located between the two parts.

Structure of Planar Portion 21

The planar portion 21 is, for example, flat. For example, the planar portion 21 has a given thickness in the height-wise direction Z and extends in the front-rear direction X and the width-wise direction Y. The planar portion 21 includes, for example, an end (here, front end) in the front-rear direction X that is connected to an upper surface of the connecting portion 24. The planar portion 21 extends, for example, straight in the front-rear direction X. The planar portion 21 extends, for example, horizontally in the front-rear direction X. The planar portion 21 has, for example, a cantilever structure in which the fixed end is the front end connected to the connecting portion 24 and the free end is a rear end located at a side opposite to the front end in the front-rear direction X.

In this specification, "the front end of the planar portion 21" refers to a region extending rearward from a front end surface of the planar portion 21 and having a given range, and "the rear end of the planar portion 21" refers to a region extending forward from a rear end surface of the planar portion 21 and having a given range. In the present embodiment, "the front end of the planar portion 21" refers to a region of the planar portion 21 in the front-rear direction X connected to the connecting portion 24.

Structure of Planar Portion 22

Figure 2:
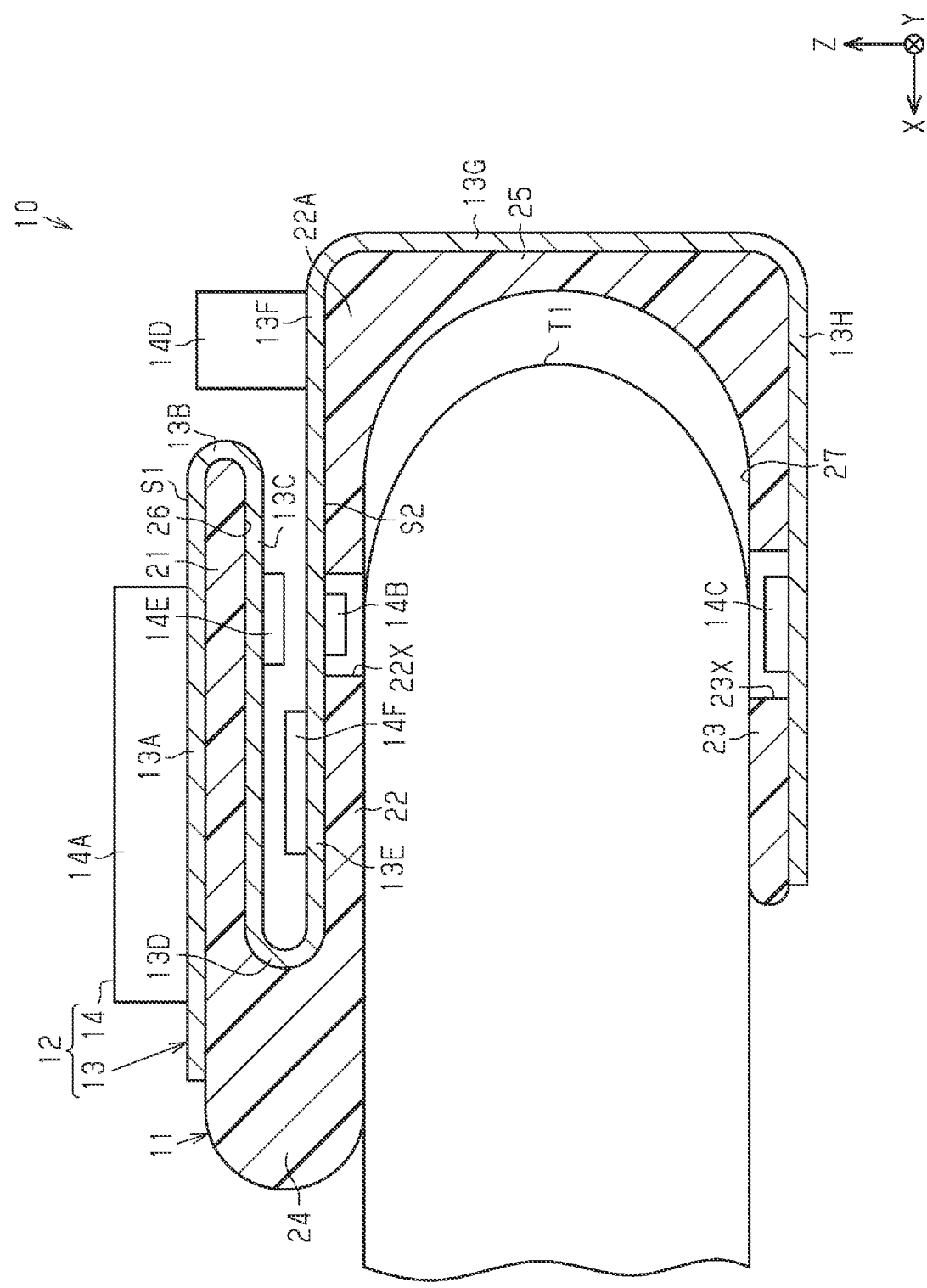
FIG. 2 is a schematic cross-sectional view illustrating an embodiment of an electronic device.

As illustrated in FIG. 2, the planar portion 22 is, for example, flat. For example, the planar portion 22 has a given thickness in the height-wise direction Z and extends in the front-rear direction X and the width-wise direction Y. The planar portion 22 includes, for example, an end (here, front end) in the front-rear direction X that is connected to a lower surface of the connecting portion 24, and the other end (here, rear end) in the front-rear direction X that is connected to an upper surface of the connecting portion 25. The planar portion 22 extends, for example, straight in the front-rear direction X. The planar portion 22 extends, for example, horizontally in the front-rear direction X. The planar portion 22 extends, for example, parallel to the planar portion 21. The planar portion 22 faces, for example, the planar portion 21 in the height-wise direction Z. The front end of the planar portion 22, for example, overlaps the front end of the planar portion 21 in plan view. The planar portion 22 is, for example, longer than the planar portion 21 in the front-rear direction X. The rear end of the planar portion 22, for example, projects rearward from the rear end surface of the planar portion 21. That is, the rear end of the planar portion 22 includes a projection 22A projecting rearward from the rear end surface of the planar portion 21 and located outside the planar portion 21 in plan view. In other words, the rear end of the planar portion 22 includes the projection 22A.

In this specification, "the front end of the planar portion 22" refers to a region extending rearward from a front end surface of the planar portion 22 and having a given range, and "the rear end of the planar portion 22" refers to a region extending forward from a rear end surface of the planar portion 22 and having a given range. In the present embodiment, "the front end of the planar portion 22" refers to a region of the planar portion 22 in the front-rear direction X connected to the connecting portion 24. In the present embodiment, "the rear end of the planar portion 22" refers to a region of the planar portion 22 in the front-rear direction X connected to the connecting portion 25.

The planar portion 22 includes, for example, a through hole 22X extending through the planar portion 22 in a thickness-wise direction (here, height-wise direction Z). The through hole 22X is located, for example, in an intermediate part of the planar portion 22 in the front-rear direction X. The planar shape of the through hole 22X is, for example, rectangular.

Structure of Connecting Portion 24

The connecting portion 24 connects, for example, the front end (first end) of the planar portion 21 and the front end (first end) of the planar portion 22. The connecting portion 24 extends, for example, from a lower surface of the front end of the planar portion 21 to an upper surface of the front end of the planar portion 22. For example, the connecting portion 24 has a given thickness in the front-rear direction X and extends in the width-wise direction Y and the height-wise direction Z. The thickness of the connecting portion 24 is, for example, greater than the thickness of each of the planar portions 21 and 22. The connecting portion 24 is, for example, curved as an arc or an ellipse. For example, the connecting portion 24 includes a front end surface and a rear end surface that are curved as an arc.

The support body 11 includes, for example, a U-shaped structural body formed by the two planar portions 21 and 22 and the connecting portion 24. The support body 11 includes, for example, a space surrounded by the lower surface of the planar portion 21, the rear end surface of the connecting portion 24, and the upper surface of the planar portion 22. The space defines a receptacle 26 into which part of the wiring substrate 13 is inserted. The lower surface (first surface) of the planar portion 21, the rear end surface (first end surface) of the connecting portion 24, and the upper surface (second surface) of the planar portion 22 define an inner surface of the receptacle 26.

Structure of Planar Portion 23

The planar portion 23 is, for example, flat. For example, the planar portion 23 has a given thickness in the height-wise direction Z and extends in the front-rear direction X and the width-wise direction Y. The planar portion 23 includes, for example, an end (here, rear end) in the front-rear direction X that is connected to a lower surface of the connecting portion 25. The planar portion 23 has, for example, a cantilever structure in which the fixed end is the rear end connected to the connecting portion 25 and the free end is a front end located at a side opposite to the rear end in the front-rear direction X. The planar portion 23 is, for example, configured to elastically deform in a direction in which the planar portions 21, 22, and 23 are arranged (here, height-wise direction Z). The planar portion 23 is, for example, configured to elastically deform and bend in the height-wise direction Z. The planar portion 23 extends, for example, straight in the front-rear direction X. The planar portion 23 extends, for example, horizontally in the front-rear direction X. The planar portion 23 extends, for example, parallel to the planar portion 22. The planar portion 23 faces, for example, the planar portion 22 in the height-wise direction Z. The rear end of the planar portion 23, for example, overlaps the rear end of the planar portion 22 in plan view. The planar portion 23 is, for example, shorter than the planar portion 22 in the front-rear direction X.

In this specification, "the front end of the planar portion 23" refers to a region extending rearward from a front end surface of the planar portion 23 and having a given range, and "the rear end of the planar portion 23" refers to a region extending forward from a rear end surface of the planar portion 23 and having a given range. In the present embodiment, "the rear end of the planar portion 23" refers to a region of the planar portion 23 in the front-rear direction X connected to the connecting portion 25.

The planar portion 23 includes, for example, a through hole 23X extending through the planar portion 23 in a thickness-wise direction (here, height-wise direction Z). The through hole 23X is located, for example, in an intermediate part of the planar portion 23 in the front-rear direction X. The through hole 23X, for example, overlaps the through hole 22X in plan view. The planar shape of the through hole 23X is, for example, rectangular. The planar shape of the through hole 23X is, for example, larger than the planar shape of the through hole 22X.

Structure of Connecting Portion 25

The connecting portion 25 connects, for example, the rear end (second end) of the planar portion 22 and the rear end (second end) of the planar portion 23. The connecting portion 25 extends, for example, from a lower surface of the rear end of the planar portion 22 to an upper surface of the rear end of the planar portion 23. The connecting portion 25 extends, for example, from a lower surface of the projection 22A to an upper surface of the rear end of the planar portion 23. For example, the connecting portion 25 has a given thickness in the front-rear direction X and extends in the width-wise direction Y and the height-wise direction Z.

The support body 11 includes, for example, a U-shaped structural body formed by the two planar portions 22 and 23 and the connecting portion 25. The support body 11 includes, for example, a space surrounded by the lower surface of the planar portion 22, a front end surface of the connecting portion 25, and the upper surface of the planar portion 23. The space defines a receptacle 27 configured to receive a measurement subject T1. The lower surface of the planar portion 22, the front end surface of the connecting portion 25, and the upper surface of the planar portion 23 define an inner surface of the receptacle 27. The gap between the lower surface of the planar portion 22 and the upper surface of the planar portion 23 is set, for example, in accordance with the thickness of the measurement subject T1. The gap between the lower surface of the planar portion 22 and the upper surface of the planar portion 23 is, for example, set to be greater than the gap between the lower surface of the planar portion 21 and the upper surface of the planar portion 22. The measurement subject T1 is, for example, a human body (living tissue). The human body includes, for example, a finger and an ear.

The support body 11 is, for example, configured to elastically deform and widen the gap between the planar portion 22 and the planar portion 23. That is, the support body 11 is configured to elastically deform and widen the space in the receptacle 27. For example, when the thickness of the measurement subject T1 is greater than the gap between the planar portion 22 and the planar portion 23 and the measurement subject T1 is inserted into the receptacle 27, the support body 11 elastically deforms to temporarily widen the gap between the planar portion 22 and the planar portion 23.

The receptacle 27 includes an outer surface. The outer surface of the receptacle 27 includes a rear end surface (first end surface) of the connecting portion 25. The rear end surface of the connecting portion 25 is, for example, flat in a direction (here, height-wise direction Z) in which the planar portion 22 and the planar portion 23 are arranged facing each other. The rear end surface of the connecting portion 25 is, for example, flat and extends vertically in the height-wise direction Z. The rear end surface of the connecting portion 25 extends, for example, in the height-wise direction Z and the width-wise direction Y. The inner surface of the receptacle 27 includes the front end surface (second end surface) of the connecting portion 25. The front end surface of the connecting portion 25 is, for example, curved as an arc or an ellipse. In the present embodiment, the front end surface of the connecting portion 25 is curved as an arc. The front end surface of the connecting portion 25 is, for example, curved and recessed from the front ends of the planar portions 22 and 23 toward the rear end surface of the connecting portion 25. That is, the front end surface of the connecting portion 25 is recessed toward an inner side of the connecting portion 25. The recess amount of the front end surface of the connecting portion 25 is, for example, increased from the planar portions 22 and 23 toward a center of the connecting portion 25 in the height-wise direction Z. In other words, the connecting portion 25 has a thickness in the front-rear direction X that is increased from the center of the connecting portion 25 in the height-wise direction Z toward the planar portions 22 and 23.

In the support body 11 of the present example, the distance in the projection 22A between the inner surface of the receptacle 27 and the outer surface of the receptacle 27 (here, upper surface of projection 22A) is greater than the distance in the planar portion 22 excluding the projection 22A between the inner surface of the receptacle 27 and the outer surface of the receptacle 27 (here, upper surface of planar portion 22).

Structure of Wiring Substrate 13

The structure of the wiring substrate 13 will be described. The wiring substrate 13 is a flexible substrate having flexibility. Flexibility refers to a property capable of bending and warping.

The wiring substrate 13 includes, for example, a mount portion 13A, a bent portion 13B, a mount portion 13C, a bent portion 13D, a mount portion 13E, a mount portion 13F, a non-mount portion 13G on which the electronic components 14 are not mounted, and a mount portion 13H. In the wiring substrate 13, for example, the mount portion 13A, the bent portion 13B, the mount portion 13C, the bent portion 13D, the mount portion 13E, the mount portion 13F, the non-mount portion 13G, and the mount portion 13H are formed continuously and integrally with each other. In this specification, a "bent portion" of the wiring substrate 13 is a portion of the wiring substrate 13 that is folded approximately 180 degrees.

Figure 3:
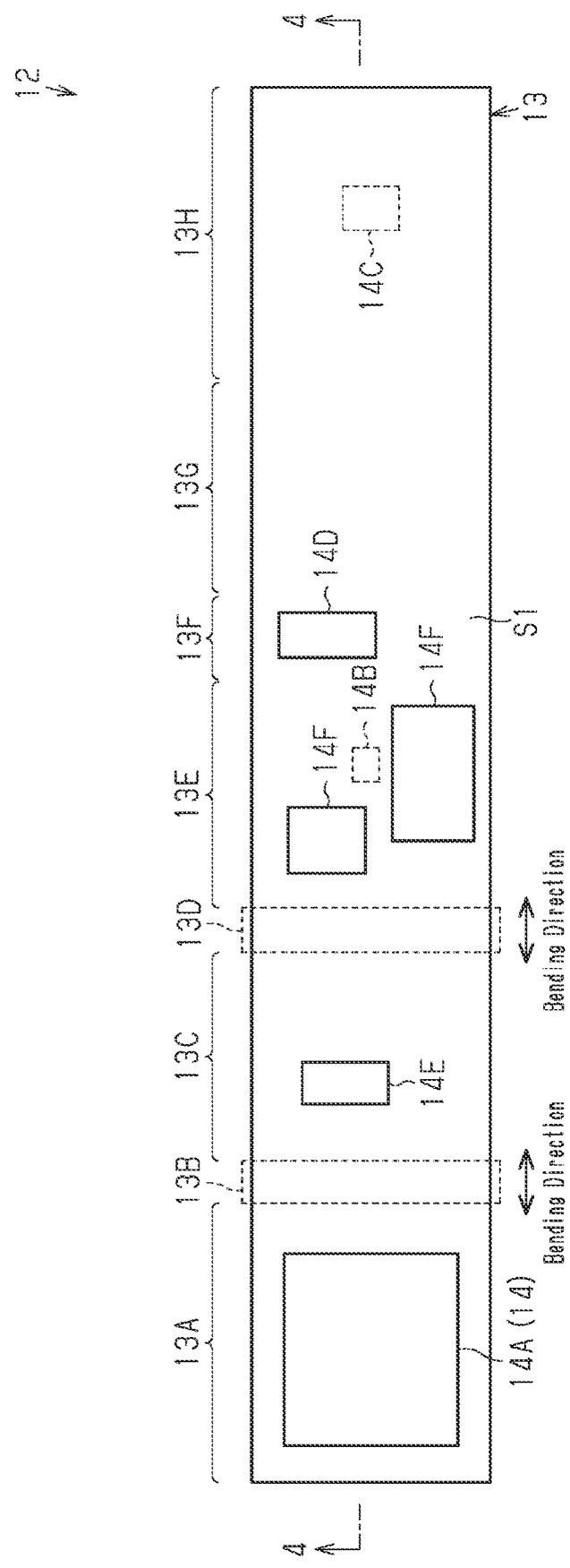
FIG. 3 is a schematic plan view illustrating an embodiment of a semiconductor device.

As illustrated in FIG. 3, the mount portion 13A, the bent portion 13B, the mount portion 13C, the bent portion 13D, the mount portion 13E, the mount portion 13F, the non-mount portion 13G, and the mount portion 13H are arranged next to one another in a longitudinal direction of the wiring substrate 13 (sideward in FIG. 3). FIG. 3 is a plan view of the semiconductor device 12 that is not attached to the support body 11, that is, the semiconductor device 12 in a state before the wiring substrate 13 is bent at the bent portions 13B and 13D. FIG. 3 is a plan view of the semiconductor device 12 as viewed from a first surface S1 (upper surface in FIG. 4) of the wiring substrate 13.

Figure 4:
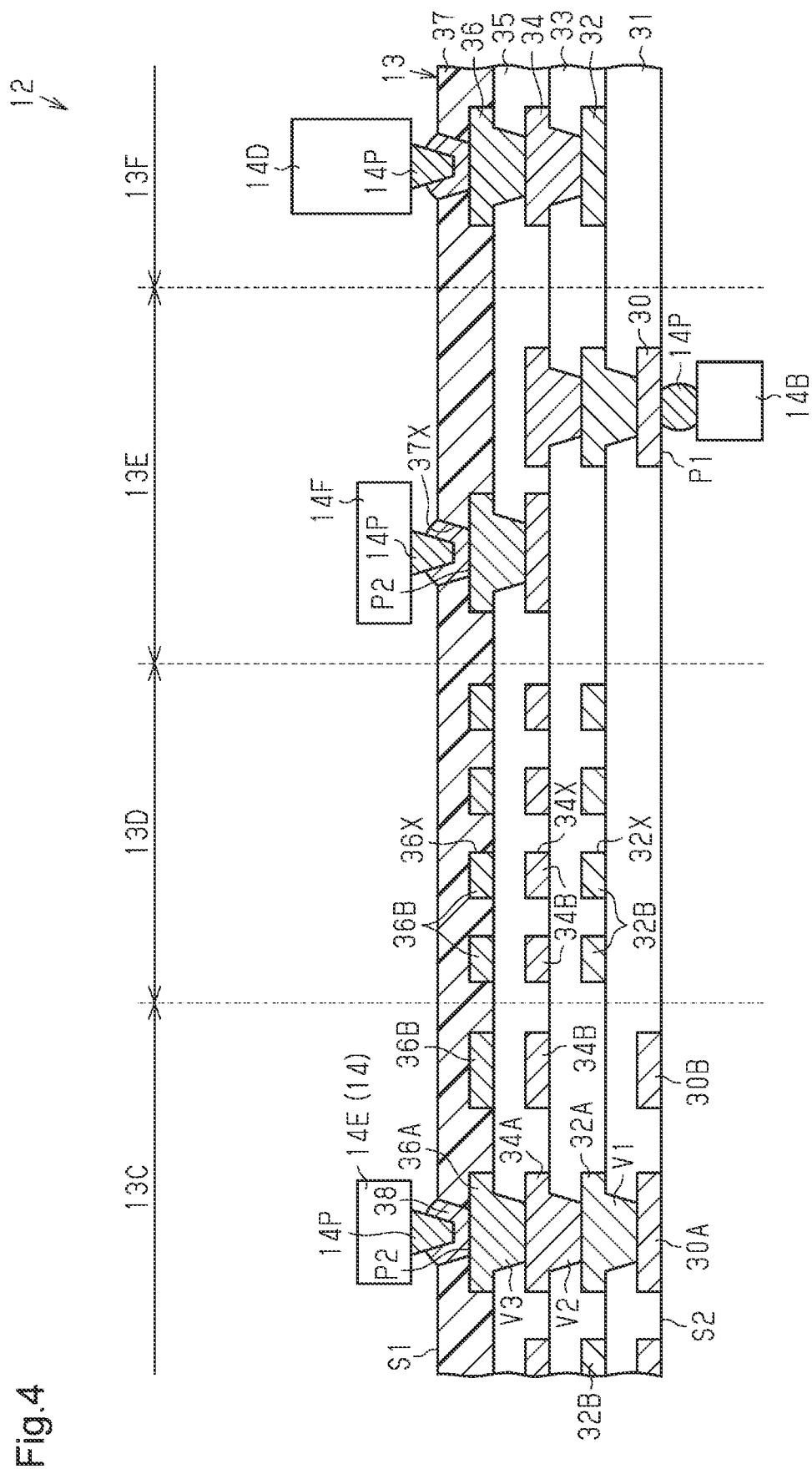
FIG. 4 is a schematic cross-sectional view illustrating the semiconductor device of the embodiment taking along line 4-4 in FIG. 3.

As illustrated in FIG. 4, some of the electronic components 14 are mounted on the first surface S1 of the wiring substrate 13, and the other electronic components 14 are mounted on a second surface S2 of the wiring substrate 13. As illustrated in FIG. 2, the second surface S2 of the wiring substrate 13 is a facing surface that faces the support body 11, and the first surface S1 of the wiring substrate 13 is an opposite surface so that the opposite surface and the second surface S2 (facing surface) are located at opposite sides of the wiring substrate 13.

As illustrated in FIG. 3, the electronic components 14 include, for example, a battery module 14A mounted on the mount portion 13A, a light emitting element 14B mounted on the mount portion 13E, a light receiving element 14C mounted on the mount portion 13H, and an antenna 14D mounted on the mount portion 13F. The electronic components 14 include, for example, an electronic component 14E mounted on the mount portion 13C and an electronic component 14F mounted on the mount portion 13E.

The battery module 14A includes, for example, a battery holder and a battery 50 (refer to FIG. 6) inserted into the battery holder. The battery 50 may be, for example, a button battery or a coil battery.

The light emitting element 14B is a photoelectric element and converts an electric signal into an optical signal. The light emitting element 14B may be, for example, a light emitting diode (LED). The light emitting element 14B includes, for example, LEDs that generate two different wavelengths. The light emitting element 14B includes, for example, a red LED that generates red light having a wavelength in the red region and an infrared LED that generates infrared light having a wavelength in the infrared region. The light receiving element 14C is a photoelectric element and converts an optical signal into an electric signal. The light receiving element 14C receives light emitted from the light emitting element 14B and generates an electric signal corresponding to the optical intensity of the received light. The light receiving element 14C may be, for example, a photodiode (PD) or a silicon photodiode.

The light receiving element 14C may be, for example, a PD that is photoresponsive to a wavelength in the red region and a wavelength in the infrared region.

The antenna 14D is used, for example, for wireless communication. The antenna 14D, for example, transmits transmission information including biometric information to an external device through wireless communication. The electronic components 14E and 14F may include, for example, a controller 52 (refer to FIG. 6) that controls the light emitting element 14B and the light receiving element 14C. Each electronic component 14 is, for example, a single IC chip or a module including multiple IC chips.

The bent portions 13B and 13D of the wiring substrate 13 are, for example, bendable portions designed assuming that the bent portions 13B and 13D will be bent in a given direction. For example, the bent portion 13B is designed assuming that the bent portion 13B will be bent in a direction in which the mount portion 13A, the bent portion 13B, the mount portion 13C are arranged (refer to illustrated arrows). For example, the bent portion 13D is designed assuming that the bent portion 13D will be bent in a direction in which the mount portion 13C, the bent portion 13D, and the mount portion 13E are arranged (refer to illustrated arrows). When including the bent portions 13B and 13D having such configurations, the wiring substrate 13 is readily bent 180 degrees at the bent portions 13B and 13D in the arrangement direction. The bending direction of the bent portions 13B and 13D conforms to the longitudinal direction of the wiring substrate 13. For example, the electronic components 14 are not mounted on the bent portions 13B and 13D.

The non-mount portion 13G connects, for example, the mount portions 13F and 13H located adjacent to each other. For example, the electronic components 14 such as the battery module 14A, the light emitting element 14B, the light receiving element 14C, the antenna 14D, and the electronic components 14E and 14F are not mounted on the non-mount portion 13G.

The structure of the semiconductor device 12 that is attached to the support body 11 will be described with reference to FIG. 2.

The wiring substrate 13 is attached to the support body 11 along the surface of the support body 11. The wiring substrate 13 is, for example, adhered to a surface of the support body 11 by an adhesive (not illustrated).

The wiring substrate 13 is attached along an upper surface (second surface) of the planar portion 21. The mount portion 13A covers the upper surface of the planar portion 21, which defines an outer surface of the receptacle 26. The battery module 14A is mounted on the first surface S1 of the mount portion 13A. The second surface S2 of the mount portion 13A faces the upper surface of the planar portion 21.

The wiring substrate 13 is folded from the upper surface of the planar portion 21 toward the inner surface of the receptacle 26 at the rear end of the planar portion 21. The wiring substrate 13 is bent approximately 180 degrees by the bent portion 13B at the rear end of the planar portion 21 and is folded from the upper surface (second surface) of the planar portion 21 toward the lower surface (first surface) of the planar portion 21. The bent portion 13B covers the rear end surface of the rear end of the planar portion 21. The bent portion 13B is, for example, curved as an arc. The bent portion 13B is, for example, folded to be U-shaped. The second surface S2 of the bent portion 13B faces the rear end surface of the rear end of the planar portion 21.

The wiring substrate 13, for example, is folded to be U-shaped along the inner surface of the receptacle 26 when attached. The mount portion 13C covers the lower surface of the planar portion 21. The electronic component 14E is mounted on the first surface S1 of the mount portion 13C facing toward the planar portion 22. The electronic component 14E projects, for example, toward the planar portion 22 (here, downward) from the first surface S1 of the mount portion 13C. The second surface S2 of the mount portion 13C faces the lower surface of the planar portion 21.

The wiring substrate 13 is folded at the rear end surface of the connecting portion 24, which defines the inner surface of the receptacle 26, and is U-shaped from the lower surface of the planar portion 21 toward the upper surface of the planar portion 22. The wiring substrate 13 is bent approximately 180 degrees by the bent portion 13D at the rear end surface of the connecting portion 24 and is folded from the lower surface of the planar portion 21 toward the upper surface of the planar portion 22. The bent portion 13D covers the rear end surface of the connecting portion 24. The bent portion 13D is, for example, curved as an arc along the rear end surface of the connecting portion 24. The bent portion 13D is, for example, folded to be U-shaped. The second surface S2 of the bent portion 13D faces the rear end surface of the connecting portion 24.

The mount portion 13E covers the upper surface of the planar portion 22. The electronic component 14F is mounted on the first surface S1 of the mount portion 13E facing toward the planar portion 21 (here, upward). The electronic component 14F projects from the first surface S1 of the mount portion 13E toward the planar portion 21 (here, upward). The electronic component 14F is, for example, configured not to contact the electronic component 14E. The electronic components 14E and 14F are arranged in the receptacle 26. The light emitting element 14B is mounted on the second surface S2 of the mount portion 13E facing toward the planar portion 22 (here, downward). The light emitting element 14B, for example, overlaps the through hole 22X of the planar portion 22 in plan view. The light emitting element 14B projects, for example, from the second surface S2 of the mount portion 13E into the through hole 22X. The light emitting element 14B is, for example, accommodated in the through hole 22X.

The wiring substrate 13 is attached along the upper surface (first surface) of the projection 22A that is continuous with the upper surface of the planar portion 22, which defines the inner surface of the receptacle 26. The mount portion 13F covers the upper surface of the projection 22A. The antenna 14D is mounted on the first surface S1 of the mount portion 13F. That is, the antenna 14D is mounted on part of the wiring substrate 13 attached to the projection 22A, namely, the first surface S1 of the mount portion 13F. In other words, the antenna 14D is located at a position that overlaps the projection 22A in plan view. The projection 22A is located outward from the receptacle 26 at a position that does not overlap the planar portion 21 in plan view. Thus, the antenna 14D mounted on the projection 22A is arranged separately from the battery module 14A, which is arranged on the planar portion 21, and the electronic components 14E and 14F and the light emitting element 14B, which are arranged in the receptacle 26. This configuration limits adverse effects on the properties of the antenna 14D caused by the battery module 14A, the light emitting element 14B, and the electronic components 14E and 14F. In addition, the distance in the projection 22A between the inner surface of the receptacle 27 and the outer surface of the receptacle 27 (here, upper surface of projection 22A) is greater than the distance in the planar portion 22 excluding the projection 22A between the inner surface of the receptacle 27 and the outer surface of the receptacle 27 (here, upper surface of planar portion 22). This configuration ensures a longer distance between the antenna 14D and the measurement subject T1 inserted into the receptacle 27 than a configuration in which the antenna 14D is arranged on the planar portion 22 other than the projection 22A. This limits adverse effects on the properties of the antenna 14D caused by the measurement subject T1 having a relatively high electric permittivity. The antenna 14D is, for example, taller than the other electronic components 14. The height of the antenna 14D is, for example, greater than the distance between the planar portion 21 and the planar portion 22. The antenna 14D, for example, overlaps the planar portion 21 from a front view in the front-rear direction. The second surface S2 of the mount portion 13F faces the upper surface of the projection 22A.

The wiring substrate 13 is attached along the rear end surface of the connecting portion 25, which defines the outer surface of the receptacle 27. The non-mount portion 13G covers the rear end surface of the connecting portion 25. The non-mount portion 13G extends, for example, straight along the rear end surface of the connecting portion 25. The non-mount portion 13G extends, for example, vertically in the height-wise direction Z. The second surface S2 of the non-mount portion 13G faces the rear end surface of the connecting portion 25.

The wiring substrate 13 is attached along the lower surface (first surface) of the planar portion 23, which defines the outer surface of the receptacle 27. The mount portion 13H covers the lower surface of the planar portion 23. The light receiving element 14C is mounted on the second surface S2 of the mount portion 13H facing toward the planar portion 23 (here, upward). The light receiving element 14C faces the light emitting element 14B. The light receiving element 14C, for example, overlaps the through hole 22X in the planar portion 22 and the through hole 23X in the planar portion 23 in plan view. The light receiving element 14C projects, for example, from the second surface S2 of the mount portion 13H into the through hole 23X. The light receiving element 14C is, for example, accommodated in the through hole 23X.

The electronic device 10 is attached to the measurement subject T1 so that the measurement subject T1 is inserted into the receptacle 27. At this time, the light emitting element 14B and the light receiving element 14C face each other and sandwich the measurement subject T1 so that transmitted light of the living body is detected. Thus, when light is emitted from the light emitting element 14B, the light is transmitted through the measurement subject T1 and received by the light receiving element 14C.

Stacking Structure of Wiring Substrate 13

The stacking structure of the wiring substrate 13 will be described with reference to FIG. 4. FIG. 4 illustrates the stacking structures in the mount portion 13C, the bent portion 13D, and the mount portions 13E and 13F. The stacking structures of the mount portion 13A, the non-mount portion 13G, and the mount portion 13H illustrated in FIG. 3 are similar to those of the mount portions 13C, 13E, and 13F and thus will not be described in detail. Also, the stacking structure of the bent portion 13B illustrated in FIG. 3 is similar to that of the bent portion 13D and thus will not be described in detail.

As illustrated in FIG. 4, the wiring substrate 13 is a multilayer wiring substrate having a structure in which wiring layers and insulation layers are alternately stacked.

The wiring substrate 13 has, for example, a structure in which a wiring layer 30, an insulation layer 31, a wiring layer 32, an insulation layer 33, a wiring layer 34, an insulation layer 35, a wiring layer 36, and a solder resist layer 37 are sequentially stacked. Thus, the wiring substrate 13 of the present embodiment differs from a wiring substrate manufactured using a typical build-up process, that is, a wiring substrate in which a desired number of build-up layers are sequentially stacked on one or both of the opposite surfaces of a core substrate as a support substrate. The wiring substrate 13 of the present embodiment is a coreless substrate that does not include a support substrate.

The material of the wiring layers 30, 32, 34, and 36 may be, for example, copper (Cu) or a copper alloy. The thickness of the wiring layers 30, 32, 34, and 36 may be, for example, approximately 10 to 20 μm. The line-and-space (L/S) of the wiring layers 30, 32, 34, and 36 may be, for example, approximately 10 μm/10 μm to 20 μm/20 μm. The line-and-space (L/S) shows the width of a wiring and the distance between adjacent wirings.

The material of the insulation layers 31, 33, and 35 may be, for example, a flexible insulative resin having a low Young's modulus. The material of the insulation layers 31, 33, and 35 may be, for example, a non-photosensitive insulative resin including a thermosetting resin such as an epoxy resin or a polyimide resin as a main component. Also, the material of the insulation layers 31, 33, and 35 may be, for example, an insulative resin including a photosensitive resin such as a phenol resin or a polyimide resin as a main component. The insulation layers 31, 33, and 35 may include, for example, a filler such as silica or alumina. The thickness of the insulation layers 31, 33, and 35 may be, for example, approximately 20 to 45 μm.

The wiring layer 30 is the outermost wiring layer (here, lowermost wiring layer) of the wiring substrate 13. The wiring layer 30 includes a wiring pattern 30A including a signal line and the like and a shield pattern 30B shielding noise such as electromagnetic noise. The shield pattern 30B is, for example, a ground pattern connected to a ground power supply (not illustrated). The insulation layer 31 is the outermost layer (here, lowermost layer) of the wiring substrate 13. In the wiring substrate 13 of the present embodiment, the lower surface of the insulation layer 31 is the second surface S2 of the wiring substrate 13. The insulation layer 31 covers side surfaces and an upper surface of the wiring layer 30 and exposes a lower surface of the wiring layer 30. The insulation layer 31 has a lower surface that is, for example, flush with the lower surface of the wiring layer 30.

The lower surface of the wiring layer 30 exposed from the insulation layer 31 is used as a connection pad P1 electrically connected to the electronic component 14. Some of the electronic components 14, namely, the light emitting element 14B and the light receiving element 14C (refer to FIG. 3), are mounted at the second surface S2 of the wiring substrate 13.

A surface-processed layer is formed on the wiring layer 30 (i.e., on the connection pad P1) exposed from the insulation layer 31 when appropriate. Examples of the surface-processed layer include a gold (Au) layer, a nickel (Ni) layer/Au layer (metal layer formed by stacking the Ni layer and the Au layer in this order), and a Ni layer/palladium (Pd) layer/Au layer (metal layer formed by stacking the Ni layer, the Pd layer, and the Au layer in this order). The Au layer is a metal layer formed of Au or an Au alloy. The Ni layer is a metal layer formed of Ni or a Ni alloy. The Pd layer is a metal layer formed of Pd or a Pd alloy. Each of the Ni layer, the Au layer, and the Pd layer may be, for example, a metal layer formed through an electroless plating process (electroless plated metal layer). In another example of the surface-processed layer, an organic solderability preservative (OSP) film may be formed on the surface of the connection pad P1 through an anti-oxidation process such as an OSP process. The OSP film may be a coating of an organic compound such as an azole compound or an imidazole compound.

The wiring layer 32 is formed on the upper surface of the insulation layer 31. The wiring layer 32 is electrically connected to the wiring layer 30 by via wirings V1 that extend through the insulation layer 31 in the thickness-wise direction. The wiring layer 32 is, for example, formed integrally with the via wirings V1. The wiring layer 32 includes a wiring pattern 32A including a signal line and the like and a shield pattern 32B shielding noise such as electromagnetic noise. The shield pattern 32B is, for example, a ground pattern connected to a ground power supply (not illustrated).

The insulation layer 33 is formed on the upper surface of the insulation layer 31 to cover the wiring layer 32. The wiring layer 34 is formed on the upper surface of the insulation layer 33. The wiring layer 34 is electrically connected to the wiring layer 32 by via wirings V2 that extend through the insulation layer 33 in the thickness-wise direction. The wiring layer 34 is, for example, formed integrally with the via wirings V2. The wiring layer 34 includes a wiring pattern 34A including a signal line and the like and a shield pattern 34B shielding noise such as electromagnetic noise. The shield pattern 34B is, for example, a ground pattern connected to a ground power supply (not illustrated).

The insulation layer 35 is formed on the upper surface of the insulation layer 33 to cover the wiring layer 34. The wiring layer 36 is formed on the upper surface of the insulation layer 35. The wiring layer 36 is electrically connected to the wiring layer 34 by via wirings V3 that extend through the insulation layer 35 in the thickness-wise direction. The wiring layer 36 is, for example, formed integrally with the via wirings V3. The wiring layer 36 includes a wiring pattern 36A including a signal line and the like and a shield pattern 36B shielding noise such as electromagnetic noise. The shield pattern 36B is, for example, a ground pattern connected to a ground or the like (not illustrated).

Each of the via wirings V1, V2, and V3 is, for example, tapered and has a width that is decreased from the upper side (side close to the solder resist layer 37) toward the lower side (side close to wiring layer 30) in FIG. 4. For example, each of the via wirings V1, V2, and V3 has the form of an inverted truncated cone so that the lower surface is smaller than the upper surface. The diameter of the upper surface of the via wirings V1, V2, and V3 may be, for example, approximately 60 to 70 μm.

The solder resist layer 37 is formed on the upper surface of the insulation layer 35 to cover the wiring layer 36. The solder resist layer 37 is the outermost layer (here, uppermost layer) of the wiring substrate 13. In the wiring substrate 13 of the present embodiment, the upper surface of the solder resist layer 37 is the first surface S1 of the wiring substrate 13. The material of the solder resist layer 37 may be, for example, an insulative resin including a photosensitive resin such as a phenol resin or a polyimide resin as a main component. The solder resist layer 37 may include, for example, a filler such as silica or alumina. The material of the solder resist layer 37 is not limited to an insulative resin including a photosensitive resin as a main component and may be, for example, the same insulative resin as used in the insulation layers 31, 33, and 35. The material of the solder resist layer 37 does not necessarily have to have a superior flexibility. When the material of the solder resist layer 37 does not have a superior flexibility, the solder resist layer 37 may be omitted from the bent portion 13D. When the solder resist layer 37 is not arranged on the bent portion 13D, the wiring layer 36 may be omitted from the bent portion 13D. The thickness of the solder resist layer 37 may be, for example, approximately 15 to 35 μm.

Openings 37X extend through the solder resist layer 37 in the thickness-wise direction and partially expose the upper surface of the wiring layer 36 as connection pads P2. The connection pads P2 are, for example, used as pads electrically connected to the electronic components 14. Some of the electronic components 14, namely, the battery module 14A (refer to FIG. 3), the antenna 14D, and the electronic components 14E and 14F, are mounted at the upper surface of the solder resist layer 37, that is, the first surface S1 of the wiring substrate 13.

A surface-processed layer is formed on the wiring layer 36 (i.e., on the connection pads P2) exposed from the openings 37X when appropriate. Examples of the surface-processed layer include a Au layer, a Ni layer/Au layer, a Ni layer/Pd layer/Au layer, and an OSP film.

In the wiring substrate 13 of the present embodiment, the number of wiring layers in the bent portion 13D is less than the number of wiring layers in the mount portions 13C, 13E, and 13F. In the mount portions 13C, 13E, and 13F and the bent portion 13D, the wiring layer 30 is located in only the mount portions 13C, 13E, and 13F. That is, the wiring layer 30 is not located in the bent portion 13D. The wiring layers 32, 34, and 36 are located in each of the mount portions 13C, 13E, and 13F and the bent portion 13D. Thus, in the wiring substrate 13 of the present example, the bent portion 13D has three layers, namely, the wiring layers 32, 34, and 36, whereas the mount portions 13C, 13E, and 13F have four layers, namely, the wiring layers 30, 32, 34, and 36. The configuration in which the bent portion 13D has a fewer number of wiring layers than the mount portions 13C, 13E, and 13F lowers the density of the wiring layers formed in the bent portion 13D and obtains a favorable flexibility.

In the present example, in the mount portions 13C, 13E, and 13F and the bent portion 13D, the via wirings V1, V2, and V3 are located in only the mount portions 13C, 13E, and 13F. That is, in the present example, the via wirings V1, V2, and V3 are not located in the bent portion 13D. Thus, the via wirings V1, V2, and V3 are not located in the bent portion 13D, which is configured to bend. The via wirings V1, V2, and V3 are located in only the mount portions 13C, 13E, and 13F, which are not expected to be bent. When the bent portion 13D is folded 180 degrees, this configuration appropriately limits occurrence of defective conductivity resulting from separation of the via wirings V1, V2, and V3.

The wiring patterns 30A, 32A, 34A, and 36A may be located in any of the mount portions 13C, 13E, and 13F and the bent portion 13D.

The shield patterns 30B, 32B, 34B, and 36B may be located in any of the mount portions 13C, 13E, and 13F and the bent portion 13D. In the wiring substrate 13 of the present example, for example, the shield patterns 32B, 34B, and 36B are formed in the mount portions 13C, 13E, and 13F and the bent portion 13D.

In the bent portion 13D, through holes 32X, 34X, and 36X respectively extend through the shield patterns 32B, 34B, and 36B in the thickness-wise direction.

Structure of Shield Patterns 32B, 34B, and 36B in Bent Portion 13D

The structure of the shield patterns 32B, 34B, and 36B located in the bent portion 13D will now be described. Here, the structure of the shield pattern 32B located in the bent portion 13D will be described. The structure of the shield patterns 34B and 36B located in the bent portion 13D is similar to that of the shield pattern 32B located in the bent portion 13D and thus will not be described in detail.

Figure 5:
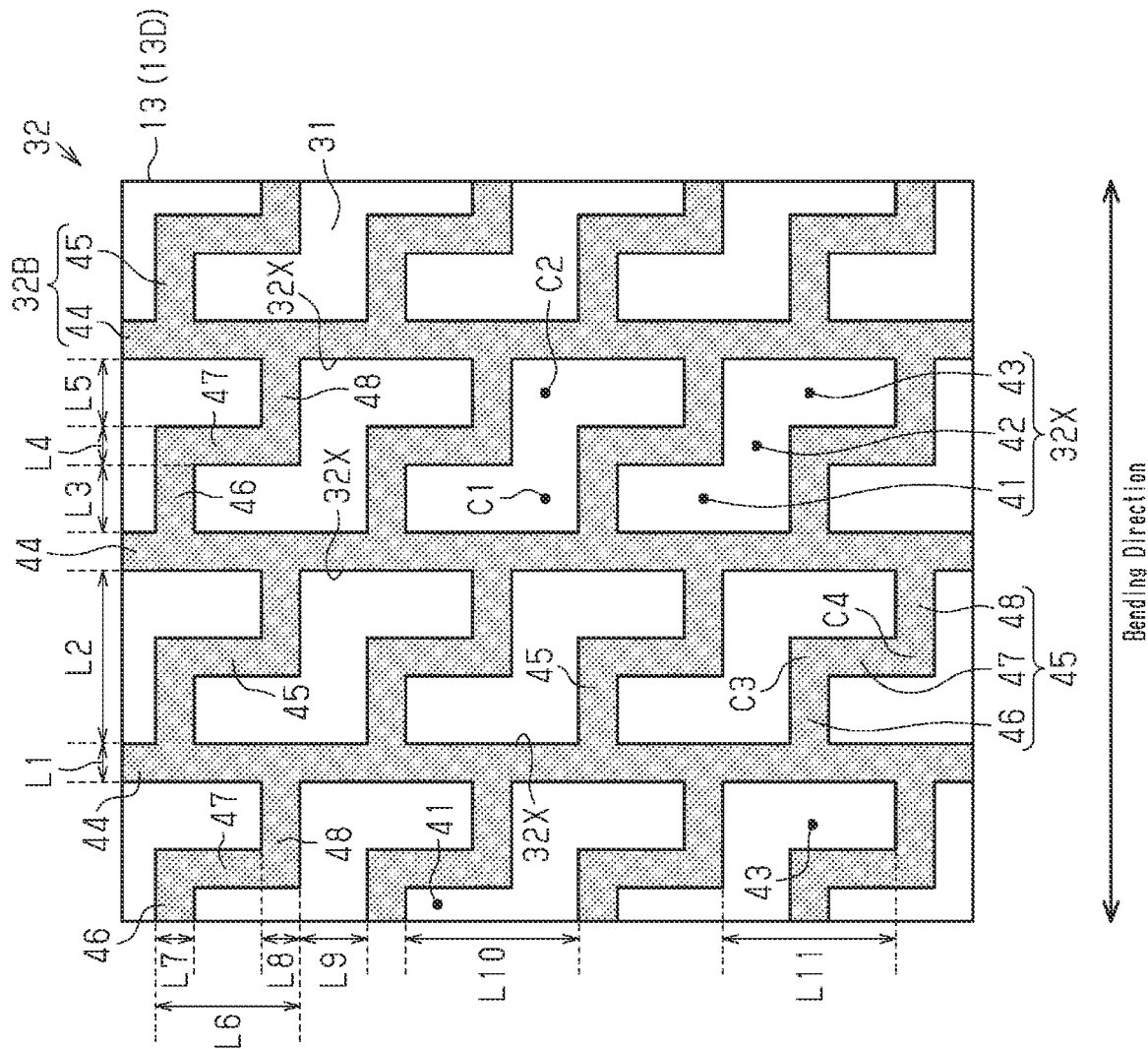
FIG. 5 is a schematic plan view illustrating an embodiment of a wiring substrate.

As illustrated in FIG. 5, the shield pattern 32B located in the bent portion 13D includes the through holes 32X. The through holes 32X are arranged at given intervals. The through holes 32X are arranged, for example, at given intervals in the bending direction and also at given intervals in a direction orthogonal to the bending direction in plan view (in the present embodiment, lateral direction of the wiring substrate 13).

The planar shape of each through hole 32X includes at least one corner. In the present example, the planar shape of the through hole 32X is crank-shaped and includes two corners C1 and C2. The through hole 32X includes an opening 41 extending in the lateral direction, which is orthogonal to the bending direction, an opening 42 extending from an end of the opening 41 in the bending direction, and an opening 43 extending from an end of the opening 42 in the lateral direction and located at a position different from the opening 42. The opening 41 and the opening 43 are, for example, the same in planar shape and size. The through holes 32X are, for example, the same in planar shape and size. The through holes 32X are, for example, arranged in the same direction. The through holes 32X define the shield pattern 32B having a grid-like structure in the bent portion 13D.

The shield pattern 32B located in the bent portion 13D includes, for example, supports 44 extending parallel to each other in a given direction and joints 45 formed between adjacent ones of the supports 44 to connect the adjacent supports 44. The joints 45 are formed, for example, continuously and integrally with the supports 44.

Each support 44, for example, extends in a direction intersecting the bending direction in plan view. In the present example, the support 44 extends in a direction (here, the lateral direction of the wiring substrate 13) orthogonal to the bending direction (here, the longitudinal direction of the wiring substrate 13). For example, the support 44 has a given width and extends in a straight direction. The supports 44 are, for example, arranged at given intervals in the bending direction. In the example illustrated in FIG. 5, three supports 44 are arranged. However, the number of supports 44 is not particularly limited. Two supports 44 may be arranged, or four or more supports 44 may be arranged.

The joints 45 are, for example, arranged at given intervals in the lateral direction of the wiring substrate 13 between adjacent ones of the supports 44. The joints 45 are, for example, arranged at given intervals in the bending direction. In the present example, the joints 45 that are arranged next to one another in the bending direction are located at the same position in the lateral direction. The joints 45 are, for example, the same in planar shape and size. The joints 45 are, for example, arranged in the same direction.

The planar shape of each joint 45 includes at least one corner. In the present example, the planar shape of each joint 45 is crank-shaped and includes two corners C3 and C4. Each joint 45 includes an extension 46 extending in the bending direction, a connector 47 extending from an end of the extension 46 in the lateral direction, which is orthogonal to the bending direction, and an extension 48 extending from an end of the connector 47 in the bending direction. That is, in the joint 45, the connector 47 is bent substantially orthogonal to the extension 46, and the extension 48 is bent substantially orthogonal to the connector 47. In the joint 45, the corner C3 is formed in the part that connects the extension 46 and the connector 47, and the corner C4 is formed in the part that connects the connector 47 and the extension 48. In the joint 45, the extension 46 and the extension 48 are located at different positions in the lateral direction. The extension 46 and the extension 48 are, for example, the same in planar shape and size. The extension 46 has an end connected to one of the adjacent supports 44. The extension 48 has an end connected to the other one of the adjacent supports 44. For example, the adjacent supports 44, the extension 46, the connector 47, and the extension 48 are formed continuously and integrally with each other.

As described above, in the shield pattern 32B located in the bent portion 13D, the planar shape of the joint 45 located between the adjacent supports 44 includes the corners C3 and C4. As a result, the joint 45 has spring-like characteristics, and a favorable flexibility is obtained from the spring-like characteristics.

The width L1 of the support 44 (i.e., dimension of the support 44 in the bending direction) may be, for example, approximately 25 to 100 μm. The distance L2 between adjacent ones of the supports 44 in the bending direction may be, for example, approximately 225 to 400 μm. The dimension L3 of the extension 46 in the bending direction may be, for example, approximately 100 to 150 μm. The width L4 of the connector 47 (i.e., dimension of the connector 47 in the bending direction) may be, for example, approximately 25 to 100 μm. The dimension L5 of the extension 48 in the bending direction may be, for example, approximately 100 to 150 μm. The dimension L6 of the entire joint 45 in the widthwise direction (i.e., dimension of the connector 47 in the lateral direction) may be, for example, approximately 201 to 350 μm. The width L7 of the extension 46 (i.e., dimension of the extension 46 in the lateral direction) may be, for example, approximately 25 to 100 μm. The width L8 of the extension 48 (dimension of the extension 48 in the lateral direction) may be, for example, approximately 25 to 100 μm. The distance L9 between adjacent ones of the joints 45 in the lateral direction may be, for example, approximately 100 to 150 μm. The distance L10 between adjacent ones of the extensions 46 in the lateral direction (i.e., dimension of the opening 41 of the through hole 32X in the lateral direction) may be, for example, approximately 126 to 500 μm. The distance L11 between adjacent ones of the extensions 48 in the lateral direction (i.e., dimension of the opening 43 of the through hole 32X in the lateral direction) may be, for example, approximately 250 to 300 μm. The dimensions of each member described above may be appropriately set based on the shield property and the flexural modulus that the shield pattern 32B is required to have.

In the present embodiment, the width L1 of the support 44, the width L4 of the connector 47, the width L7 of the extension 46, and the width L8 of the extension 48 are set to be the same. In addition, in the present embodiment, the distance L2 between the adjacent supports 44 in the bending direction is set to be greater than the distance L10 between the adjacent extensions 46 in the lateral direction (or the distance L11 between the adjacent extensions 48 in the lateral direction). Thus, the distance between the supports 44, which have a higher rigidity than the joints 45, is increased to ensure a favorable flexibility.

Although the details are not illustrated in FIG. 4, the shield patterns 34B and 36B located in the bent portion 13D include the through holes 34X and 36X that have the same planar shape as the through holes 32X. For example, the through holes 34X and 36X are the same in size as the through holes 32X and are arranged at the same intervals as the through holes 32X. In the present embodiment, the through holes 32X, 34X, and 36X that are adjacent to each other in the stacking direction overlap in plan view.

Each of the shield patterns 32B, 34B, and 36B located in the bent portion 13D has an area such that the shield patterns 32B, 34B, and 36B maintain required shield properties. When the material of the shield patterns 32B, 34B, and 36B is copper, the copper remaining rate of each of the shield patterns 32B, 34B, and 36B located in the bent portion 13D may be set in any manner within a range allowing for the continuity of the required shield properties. For example, the copper remaining rate of the shield patterns 32B, 34B, and 36B located in the bent portion 13D may be set to approximately 30% to 40%. The copper remaining rate refers to the rate of the area of a copper layer occupied on an insulation layer.

As illustrated in FIG. 4, the electronic components 14 include, for example, electrode terminals 14P arranged on one surface of the electronic components 14. The electrode terminals 14P may be, for example, metal posts, gold bumps, or solder bumps. The material of the metal posts may be, for example, copper or a copper alloy. The material of the solder bumps may be, for example, an alloy including lead (Pb), an alloy of tin (Sn) and Cu, an alloy of Sn and silver (Ag), or an alloy of Sn, Ag, and Cu.

In the light emitting element 14B, for example, the electrode terminal 14P is electrically connected to the connection pad P1 of the wiring substrate 13. Thus, the light emitting element 14B is electrically connected to the wiring pattern 30A of the wiring substrate 13 by the electrode terminal 14P. That is, the light emitting element 14B is flip-chip-mounted on the second surface S2 of the wiring substrate 13. In the antenna 14D and the electronic components 14E and 14F, for example, the electrode terminals 14P are electrically connected to the connection pads P2 of the wiring substrate 13. The electrode terminals 14P are electrically connected to the connection pads P2 by, for example, solder 38 arranged on the connection pads P2. Thus, the antenna 14D and the electronic components 14E and 14F are electrically connected to the wiring pattern 36A of the wiring substrate 13 by the electrode terminals 14P and the solder 38. That is, the antenna 14D and the electronic components 14E and 14F are flip-chip-mounted on the first surface S1 of the wiring substrate 13. The material of the solder 38 may be, for example, an alloy including Pb, an alloy of Sn and Cu, an alloy of Sn and Ag, or an alloy of Sn, Ag, and Cu.

Although the details are not illustrated in FIG. 3, the battery module 14A is flip-chip-mounted on the first surface S1 of the wiring substrate 13 in the same manner as the antenna 14D and the electronic components 14E and 14F. Also, the light receiving element 14C illustrated in FIG. 3 is also flip-chip-mounted on the second surface S2 of the wiring substrate 13 in the same manner as the light emitting element 14B.

Electric Configuration of Electronic Device 10

The electric configuration of the electronic device 10 will now be described with reference to FIG. 6.

Figure 6:
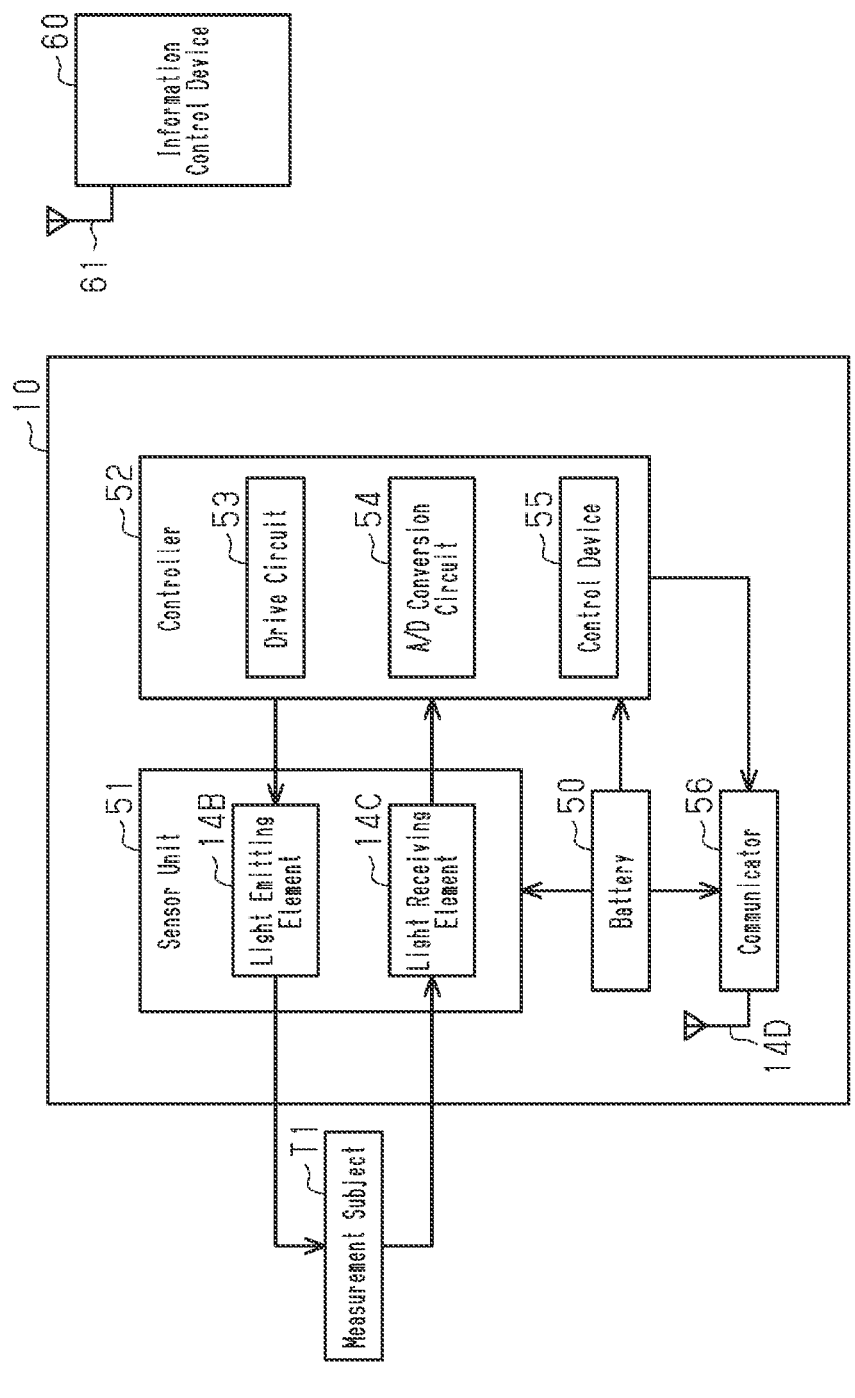
FIG. 6 is a block diagram illustrating electric configurations of an embodiment of an electronic device.

As illustrated in FIG. 6, the electronic device 10 configures a biometric information measurement system, for example, in cooperation with an information control device 60.

The electronic device 10 includes, for example, the battery 50, a sensor unit 51, the controller 52, and a communicator 56.

The battery 50 is, for example, configured to supply power to the sensor unit 51, the controller 52, and the communicator 56 so that the sensor unit 51, the controller 52, and the communicator 56 are operated by the power.

The sensor unit 51 is configured to detect biometric information of the measurement subject T1 of an examinee and output a signal corresponding to the biometric information. The sensor unit 51 may be configured in various modes in accordance with, for example, biometric information that is obtained. When an electrocardiogram or impedance respiration is obtained as biometric information, the sensor unit 51 includes electrodes that detect bioelectric potential. When thermistor respiration or body temperature is obtained as biometric information, the sensor unit 51 includes a temperature detection element. When a blood sugar level is obtained as biometric information, the sensor unit 51 includes a blood sugar level detection element. When a pulse rate or a blood oxygen saturation level is obtained as biometric information, the sensor unit 51 includes a light emitting element and a light receiving element. In the present embodiment, the sensor unit 51 is configured to obtain the blood oxygen saturation level as biometric information and has the light emitting element 14B and the light receiving element 14C.

The controller 52 is electrically connected to the light emitting element 14B and the light receiving element 14C. The controller 52 is electrically connected to the communicator 56.

The controller 52 includes, for example, a drive circuit 53 that drives the light emitting element 14B, an A/D conversion circuit 54 that converts an analog signal into a digital signal, and a control device 55. The drive circuit 53 is, for example, configured to execute control that causes the light emitting element 14B to emit light based on a given sampling cycle. The light emitted from the light emitting element 14B is, for example, transmitted through the measurement subject T1 inserted into the receptacle 27 (refer to FIG. 2) and received by the light receiving element 14C. The A/D conversion circuit 54, for example, obtains biometric information (analog signal) output from the light receiving element 14C in synchronization with light emission of the light emitting element 14B and converts the obtained analog signal into a digital signal. The control device 55 is, for example, configured to centrally control operation of each circuit in the controller 52. The control device 55, for example, executes a given analysis process on the digital signal (i.e., biometric information) generated in the A/D conversion circuit 54 and generates analysis result information. The control device 55, for example, transmits the digital signal (i.e., biometric information) generated in the A/D conversion circuit 54 or the analysis result information to the communicator 56.

The control device 55 may be configured to be circuitry that includes [1] one or more processors that execute various processes in accordance with computer programs (software), [2] one or more dedicated hardware circuits that execute at least some of various processes such as application specific integrated circuits (ASICs), or [3] a combination of these. The processor includes a central processing unit (CPU) and memory such as random access memory (RAM) and read only memory (ROM).

The memory stores program codes or instructions configured to cause the CPU to execute processes. The memory, or a computer readable medium, includes any type of medium that is accessible by a general-purpose computer or a dedicated computer.

The communicator 56 is connected to the antenna 14D so as to communicate with the information control device 60 in accordance with a given wireless communication method. The communicator 56 is, for example, a transmission circuit. The communicator 56 transmits transmission information including biometric information obtained by the light emitting element 14B and the light receiving element 14C and the analysis result information to the antenna 14D. The communicator 56 transmits the transmission information from the antenna 14D to the information control device 60 through wireless communication. Examples of wireless communication methods include Bluetooth low energy (BLE) (Bluetooth is registered trademark), ZigBee (registered trademark), ANT+ (registered trademark), and NFC.

The information control device 60 includes, for example, an antenna 61 and receives information transmitted from the electronic device 10. The information control device 60, for example, stores the received information in a storage device. The storage device may be, for example, a hard disk drive (HDD).

The information control device 60, for example, shows the received information on a display. The information control device 60, for example, displays an analysis result, which is obtained by executing a given analysis process on the received information, on the display. The display may be, for example, a liquid crystal display or an organic electronic luminescence (EL).

Manufacturing Method of Semiconductor Device 12

The method for manufacturing the semiconductor device 12 will now be described with reference to FIGS. 7 to 12. In the present embodiment, a single semiconductor device is individually manufactured on a support substrate, and then the support substrate is removed. However, a portion that will become multiple semiconductor devices may be manufactured on a support substrate and the support substrate may be removed, and the portion may be singulated into the semiconductor devices. To facilitate understanding, portions that ultimately become elements of the semiconductor device 12 are indicated by reference characters used to denote the final elements. A structural body of the mount portions 13C, 13E, and 13F and the bent portion 13D will be illustrated and described.

Figure 7A:
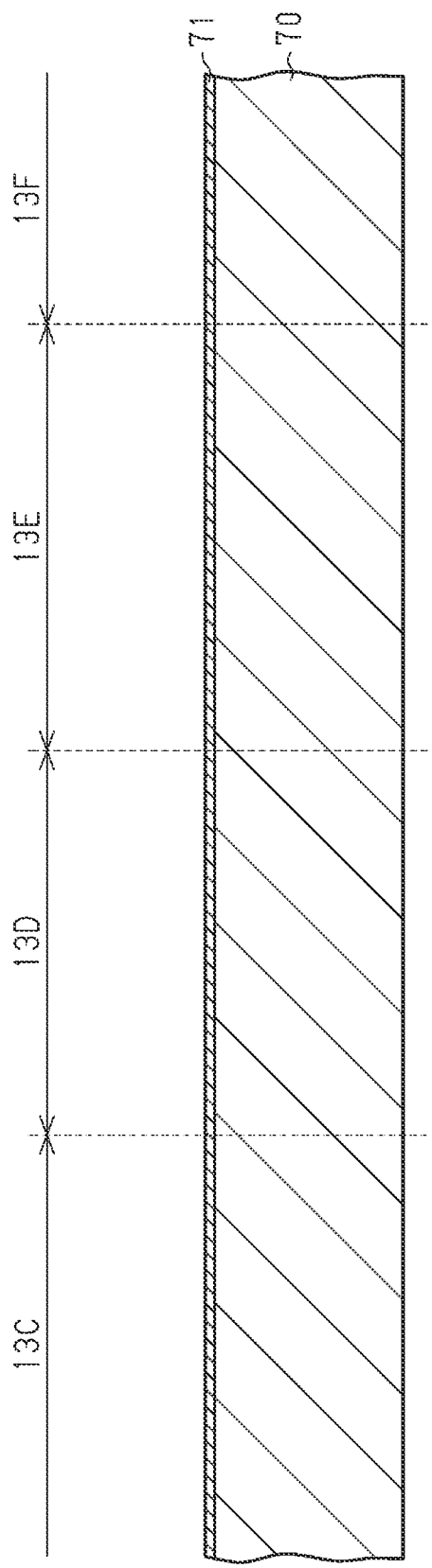

As illustrated in FIG. 7A, a support substrate 70 is prepared. The support substrate 70 may be, for example, a metal plate or a metal foil. In the present embodiment, for example, a copper foil is used. The thickness of the support substrate 70 may be, for example, approximately 18 to 100 μm.

Then, a seed layer 71 is formed on the upper surface of the support substrate 70 to cover the entire upper surface of the support substrate 70. The seed layer 71 may be formed, for example, through an electroless plating process (e.g., electroless copper plating method) or sputtering. The material of the seed layer 71 may be, for example, a conductive material used as a stopper layer when the support substrate 70 is removed by etching. The material of the seed layer 71 may be a conductive material that allows for selective etching removal of the support substrate 70. Such a material of the seed layer 71 may be, for example, a metal such as nickel (Ni), titanium (Ti), chromium (Cr), tin, cobalt (Co), or palladium or an alloy including at least one kind of metal selected from these metals.

Figure 7B:
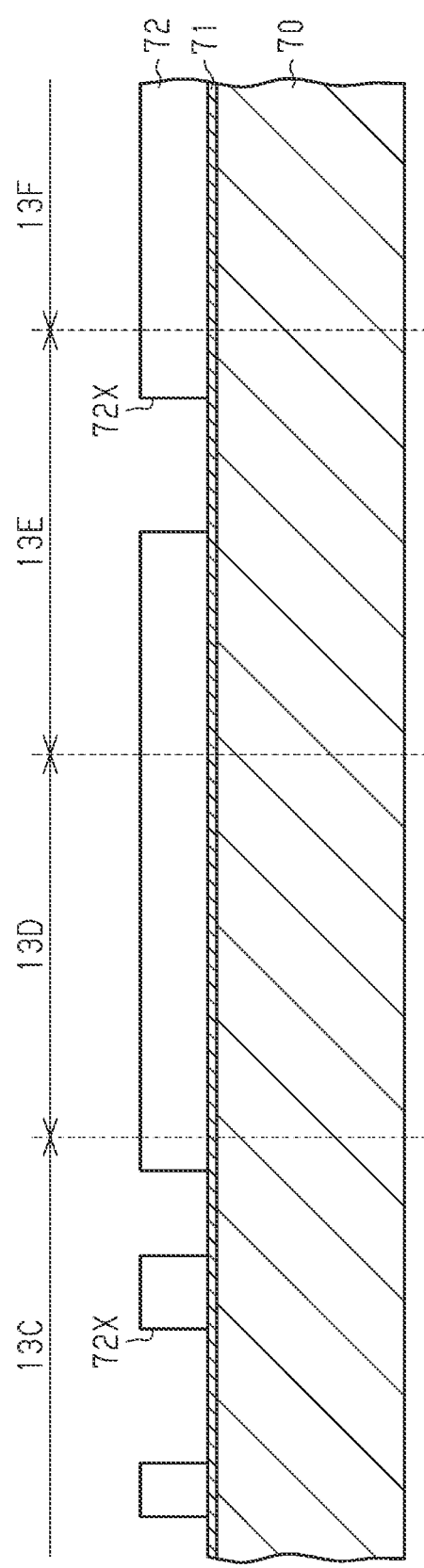

In the step illustrated in FIG. 7B, a resist layer 72 including an open pattern 72X is formed on the upper surface of the seed layer 71. The open pattern 72X exposes a portion of the upper surface of the seed layer 71 corresponding to the formation region of the wiring layer 30 (refer to FIG. 4). The material of the resist layer 72 may be, for example, a photosensitive dry film resist or a liquid photoresist (e.g., dry film resist or liquid resist of novolac resin or acrylic resin). For example, when a photosensitive dry film resist is used, the upper surface of the seed layer 71 is laminated with a dry film through thermocompression bonding, and the dry film is patterned through photolithography to form the resist layer 72. When a liquid photoresist is used, the resist layer 72 may also be formed by the same steps.

In the step illustrated in FIG. 8A, a conductive layer 73 is formed on the upper surface of the seed layer 71 exposed from the open pattern 72X in the resist layer 72. For example, as the resist layer 72 is used as a plating mask, the upper surface of the seed layer 71 exposed from the open pattern 72X undergoes an electrolytic plating process (e.g., electrolytic copper plating process) that uses the seed layer 71 as a plating power feeding layer, so that the conductive layer 73 is formed on the seed layer 71.

The resist layer 72 is removed, for example, by an alkaline stripping solution (e.g., organic amine stripping solution, caustic soda, acetone, or ethanol).

In the step illustrated in FIG. 8B, as the conductive layer 73 is used as an etching mask, an unwanted portion of the seed layer 71 is etched and removed. As a result, the wiring layer 30 including the seed layer 71 and the conductive layer 73 is formed. The wiring layer 30 includes the wiring pattern 30A and the shield pattern 30B. The wiring layer 30 is not formed on the bent portion 13D. In FIGS. 9 to 12, the seed layer 71 and the conductive layer 73 are not illustrated and are illustrated as the wiring layer 30 (the wiring pattern 30A and the shield pattern 30B).

In the step illustrated in FIG. 9A, the insulation layer 31 is formed on the upper surface of the support substrate 70 to cover the wiring layer 30. When a resin film is used as the insulation layer 31, for example, after the support substrate 70 is laminated with the resin film, the resin film may be heated under pressure at a temperature of approximately 130° C. to 190° C. so that the resin is cured to form the insulation layer 31. Alternatively, a liquid or paste of an insulative resin may be applied to the upper surface of the support substrate 70 through a spin coating process or the like, and the applied insulative resin may be heated and cured at a temperature of approximately 130° C. to 190° C. to form the insulation layer 31.

In the step illustrated in FIG. 9B, via holes 31X are formed in the insulation layer 31 to extend through the insulation layer 31 in the thickness-wise direction and partially expose the upper surface of the wiring layer 30. In the mount portions 13C, 13E, and 13F and the bent portion 13D, the via holes 31X are formed in only the mount portions 13C, 13E, and 13F. The via holes 31X may be formed, for example, by laser cutting using a $CO_2$ laser or a YAG laser. When the insulation layer 31 is formed of a photosensitive resin, the desired via holes 31X may be formed, for example, through photolithography.

When the via holes 31X are formed by laser cutting, a desmear process is performed to remove resin smears from the surface of the wiring layer 30 exposed in the bottom of the via holes 31X.

In the step illustrated in FIG. 10A, the via holes 31X are filled with a via conductor to form the via wirings V1, and the wiring layer 32 is formed on the upper surface of the insulation layer 31 and electrically connected to the wiring layer 30 by the via wirings V1. The via wirings V1 and the wiring layer 32 may be formed using, for example, various wiring forming processes such as a semi-additive process or a subtractive process. The wiring layer 32 includes the wiring pattern 32A and the shield pattern 32B. At this time, the shield pattern 32B located in the bent portion 13D includes the through holes 32X having the planar shape including the corners C1 and C2 (refer to FIG. 5).

In the step illustrated in FIG. 10B, in the same manner as the steps illustrated in FIGS. 9A and 9B, the insulation layer 33 is formed on the upper surface of the insulation layer 31 and includes via holes 33X partially exposing the upper surface of the wiring layer 32.

In the same manner as the step illustrated in FIG. 10A, the via holes 33X are filled with a via conductor to form the via wirings V2, and the wiring layer 34 is formed on the upper surface of the insulation layer 33 and electrically connected to the wiring layer 32 by the via wirings V2. The wiring layer 34 includes the wiring pattern 34A and the shield pattern 34B. At this time, the shield pattern 34B located in the bent portion 13D includes the through holes 34X having the planar shape including the corners C1 and C2 (refer to FIG. 5).

In the step illustrated in FIG. 11, in the same manner as the steps illustrated in FIGS. 9A and 9B, the insulation layer 35 is formed on the upper surface of the insulation layer 33 and includes via holes 35X partially exposing the upper surface of the wiring layer 34.

In the same manner as the step illustrated in FIG. 10A, the via holes 33X are filled with a via conductor to form the via wirings V3, and the wiring layer 36 is formed on the upper surface of the insulation layer 35 and electrically connected to the wiring layer 34 by the via wirings V3. The wiring layer 36 includes the wiring pattern 36A and the shield pattern 36B. At this time, the shield pattern 36B located in the bent portion 13D includes the through holes 36X having the planar shape including the corners C1 and C2 (refer to FIG. 5).

The solder resist layer 37, which includes the openings 37X partially exposing the upper surface of the wiring layer 36 as the connection pads P2, is formed on the upper surface of the insulation layer 35. The solder resist layer 37 may be formed, for example, by laminating a photosensitive solder resist film or applying a liquid solder resist and patterning the resist through photolithography. A surface-processed layer may be formed on the connection pads P2 when appropriate.

Figure 12:
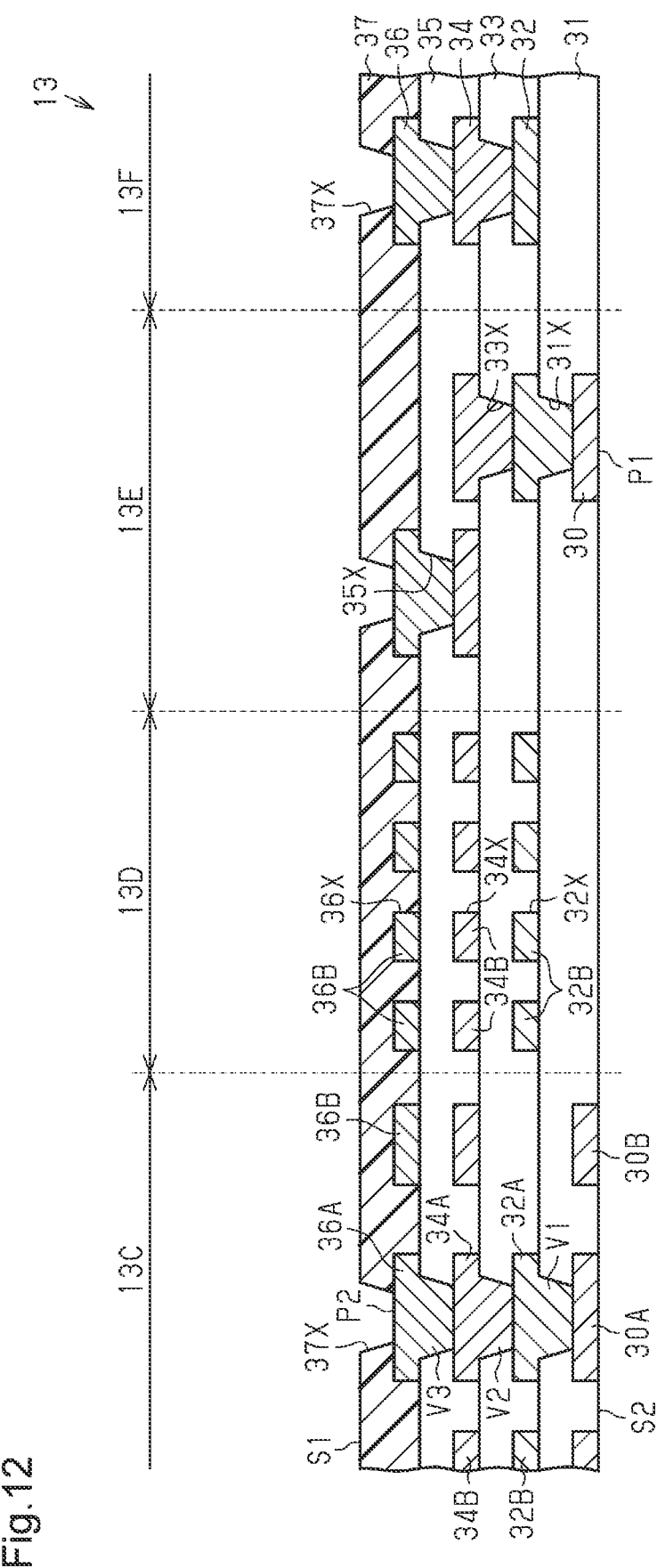

Then, the support substrate 70 is removed. When a copper foil is used as the support substrate 70, the support substrate 70 may be removed, for example, by wet etching that uses a ferric chloride aqueous solution, a cupric chloride aqueous solution, or an ammonium persulfate aqueous solution. As a result of this step, as illustrated in FIG. 12, the lower surface of the wiring layer 30 is exposed from the insulation layer 31 as the connection pad P1. A surface-processed layer may be formed on the connection pad P1 when appropriate.

The steps described above manufacture the wiring substrate 13 of the present embodiment. Subsequently, the electronic components 14 are mounted on the first surface S1 and the second surface S2 of the wiring substrate 13, so that the semiconductor device 12 illustrated in FIG. 4 is manufactured.

The present embodiment has the advantages described below.

(1) The light emitting element 14B is mounted on the second surface S2 of the mount portion 13E of the wiring substrate 13 attached to the inner surface of the receptacle 26, and the antenna 14D is mounted on the first surface S1 of the mount portion 13F of the wiring substrate 13 attached to the upper surface of the projection 22A. The projection 22A projects outward from the receptacle 26 and is located outside the planar portion 21 in plan view. Thus, the antenna 14D arranged on the projection 22A is arranged separately from the light emitting element 14B mounted on the mount portion 13E, which is arranged in the receptacle 26. In addition, the antenna 14D is arranged separately from the electronic components 14E and 14F arranged in the receptacle 26. This configuration limits adverse effects on the properties of the antenna 14D caused by the light emitting element 14B and the electronic components 14E and 14F if the light emitting element 14B and the electronic components 14E and 14F are located close to the antenna 14D.

(2) The antenna 14D is arranged separately from the light emitting element 14B, which is a sensor element that detects biometric information of an examinee, so that the antenna 14D is located at a position away from the measurement subject T1. In this configuration, the measurement subject T1, that is, a human body having a relatively high electric permittivity, will not be located close to the antenna 14D. This limits adverse effects on the properties of the antenna 14D caused by the measurement subject T1.

(3) The support body 11 includes the receptacle 27 configured to receive the measurement subject T1. In this configuration, when the measurement subject T1 is inserted into the receptacle 27, the electronic device 10 is attached to the examinee. Thus, the electronic device 10 is readily attached to the examinee.

(4) The distance in the projection 22A between the inner surface of the receptacle 27 and the outer surface of the receptacle 27 (here, upper surface of projection 22A) is greater than the distance in the planar portion 22 excluding the projection 22A between the inner surface of the receptacle 27 and the outer surface of the receptacle 27 (here, upper surface of planar portion 22). This configuration ensures a longer distance between the antenna 14D and the measurement subject T1 inserted into the receptacle 27 than a configuration in which the antenna 14D is arranged on the planar portion 22 other than the projection 22A. This appropriately limits adverse effects on the properties of the antenna 14D caused by the measurement subject T1 having a relatively high electric permittivity.

(5) The front end surface of the connecting portion 25, which defines the inner surface of the receptacle 27, is curved to have a recess amount that is increased from the planar portion 22 toward the center of the connecting portion 25 in the height-wise direction. This increases the distance in the projection 22A between the inner surface of the receptacle 27 and the outer surface of the receptacle 27. In this configuration, a curved surface is formed on the front end surface of the connecting portion 25, which may contact the tip of the measurement subject T1, while restricting an approach of the measurement subject T1 toward the antenna 14D.

(6) The light emitting element 14B is accommodated in the through hole 22X of the planar portion 22, and the light receiving element 14C is accommodated in the through hole 23X of the planar portion 23. In this configuration, the through holes 22X and 23X, which are thickness-wise spaces in the planar portions 22 and 23, are utilized as the accommodation portions for the light emitting element 14B and the light receiving element 14C. This limits enlargement of the electronic device 10 as compared to a configuration in which the light emitting element 14B and the light receiving element 14C are arranged at positions other than the through holes 22X and 23X.

(7) The battery module 14A is mounted on the mount portion 13A, which covers the upper surface of the planar portion 21 defining the outer surface of the receptacle 26. The projection 22A is located at a position that does not overlap the planar portion 21 in plan view. That is, the projection 22A is located outside the planar portion 21 in plan view. Thus, the antenna 14D, which is arranged on the projection 22A, is arranged separately from the battery module 14A, which is arranged on the planar portion 21. This limits adverse effects on the properties of the antenna 14D caused by the battery module 14A if the battery module 14A is located close to the antenna 14D.

(8) The through holes 32X having a planar shape including the corners C1 and C2 are arranged at given intervals in the shield pattern 32B located in the bent portions 13B and 13D. This configuration decreases the flexural modulus of the shield pattern 32B and the flexural modulus of the bent portions 13B and 13D as compared to a configuration in which a shield pattern is a solid pattern and does not include a through hole. As a result, the flexibility of the bent portions 13B and 13D is improved.

(9) When the through holes 32X are formed in the shield pattern 32B, the corners C3 and C4 are formed on the shield pattern 32B defined by the through holes 32X. The shield pattern 32B having the corners C3 and C4 obtains spring-like characteristics, and a favorable flexibility is obtained from the spring-like characteristics.

(10) The shield pattern 32B includes the supports 44 extending parallel to each other in a direction orthogonal to the bending direction and the joints 45 formed between adjacent ones of the supports 44. In addition, the planar shape of each joint 45 has the corners C3 and C4. As a result, the joint 45 has spring-like characteristics, and a favorable flexibility is obtained from the spring-like characteristics.

(11) The supports 44 extend in a direction orthogonal to the bending direction. In this configuration, the supports 44, which have a higher rigidity than the joints 45, extend in a direction orthogonal to the bending direction. This appropriately limits interference of the supports 44 with the flexibility of the bent portions 13B and 13D.

(12) The entirety of the joints 45 extend in the bending direction. In this configuration, the joints 45, which have a lower rigidity than the supports 44 and have spring-like characteristics, extend in the bending direction. This effectively decreases the flexural modulus of the bent portions 13B and 13D and further improves the flexibility of the bent portions 13B and 13D.

(13) In the bent portions 13B and 13D, the through holes 32X, 34X, and 36X arranged in the shield patterns 32B, 34B, and 36B that are adjacent to each other in the stacking direction overlap each other in plan view. In this configuration, since the through holes 32X, 34X, and 36X located adjacent to each other in the stacking direction overlap with each other in plan view, gas is readily removed through the through holes 32X, 34X, and 36X. Thus, the through holes 32X, 34X, and 36X are used as degassing holes. The through holes 32X, 34X, and 36X used as degassing holes limit formation of voids in the wiring substrate 13. The degassing hole is a hole used to release gas from the wiring substrate during a process of manufacturing the wiring substrate in which the wiring substrate is heated and the gas is generated.

It should be apparent to those skilled in the art that the foregoing embodiments may be implemented in many other specific forms without departing from the scope of this disclosure. Particularly, it should be understood that the foregoing embodiments may be implemented in the following forms.

The embodiment may be modified as follows. The embodiment and the following modified examples can be combined as long as the combined modified examples remain technically consistent with each other.

In the embodiment, the front end surface of the connecting portion 25, which defines the inner surface of the receptacle 27, is curved to have a recess amount that is increased from the planar portion 22 toward the center of the connecting portion 25 in the height-wise direction. This increases the distance in the projection 22A between the inner surface of the receptacle 27 and the outer surface of the receptacle 27. However, the specific configuration is not particularly limited as long as the distance in the projection 22A between the inner surface of the receptacle 27 and the outer surface of the receptacle 27 is greater than the distance in the planar portion 22 excluding the projection 22A between the inner surface of the receptacle 27 and the outer surface of the receptacle 27.

In the embodiment, the distance in the projection 22A between the inner surface of the receptacle 27 and the outer surface of the receptacle 27 is greater than the distance in the planar portion 22 excluding the projection 22A between the inner surface of the receptacle 27 and the outer surface of the receptacle 27. However, there is no limitation to such a configuration. For example, the distance in the projection 22A between the inner surface of the receptacle 27 and the outer surface of the receptacle 27 may be set to be equal to the distance in the planar portion 22 excluding the projection 22A between the inner surface of the receptacle 27 and the outer surface of the receptacle 27.

In the embodiment, the rear end surface of the connecting portion 25, which defines the outer surface of the receptacle 27, is flat in the height-wise direction Z. However, there is no limitation to such a configuration. For example, the rear end surface of the connecting portion 25 may be curved as an arc.

Figure 13:
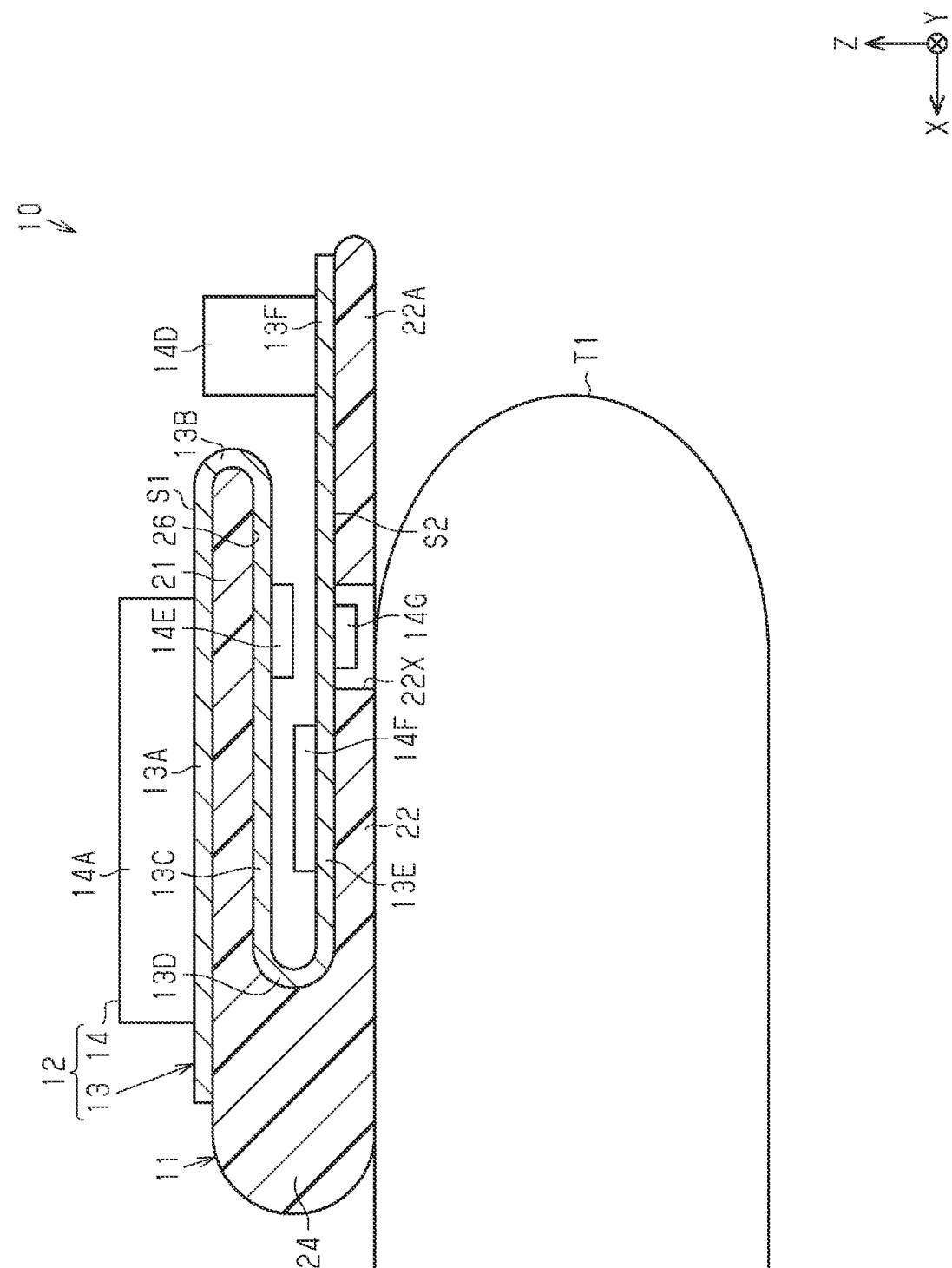
FIG. 13 is a schematic cross-sectional view illustrating a modified example of an electronic device.

As illustrated in FIG. 13, the connecting portion 25 and the planar portion 23 may be omitted from the support body 11. In this case, the receptacle 27 is omitted from the support body 11. In this case, the support body 11 is formed by the planar portions 21 and 22 and the connecting portion 24. Even in this case, the planar portion 22 includes the projection 22A projecting outward from the receptacle 26. The antenna 14D is mounted on the mount portion 13F of the wiring substrate 13 covering the upper surface of the projection 22A. In addition, a sensor element 14G is mounted on the second surface S2 of the mount portion 13E of the wiring substrate 13, which covers the upper surface of the planar portion 22 defining the inner surface of the receptacle 26. The sensor element 14G is, for example, accommodated in the through hole 22X of the planar portion 22. The sensor element 14G may be, for example, a light emitting element, a light receiving element, a temperature detection element, or a blood sugar level detection element. In this case, the non-mount portion 13G and the mount portion 13H are omitted from the wiring substrate 13.

In the modified example illustrated in FIG. 13, the mount position of the sensor element 14G is not particularly limited. For example, the mount position of the sensor element 14G may be any position of a portion of the wiring substrate 13 that is attached to the inner surface of the receptacle 26. The sensor element 14G may be mounted on, for example, the mount portion 13C of the wiring substrate 13 covering the lower surface of the planar portion 21.

In the embodiment, the mount portion 13A and the bent portion 13B may be omitted from the wiring substrate 13.

In the embodiment, the battery module 14A may be omitted from the electronic device 10. In this case, the electronic device 10 may be supplied with power from a power supply device arranged outside the electronic device 10, and the electronic device 10 may be actuated by the power.

In the semiconductor device 12 of the embodiment, the number of electronic components 14 and mount positions of the electronic components 14 are not particularly limited. For example, the light receiving element 14C may be mounted on the second surface S2 of the mount portion 13E, and the light emitting element 14B may be mounted on the second surface S2 of the mount portion 13H. For example, the electronic component 14 may be mounted on the non-mount portion 13G.

In the embodiment, the mounting mode (e.g., flip-chip-mounting, wire-bonding mounting, solder mounting, or combination of these) of the electronic components 14 in the semiconductor device 12 may be appropriately changed.

In the embodiment, the structure of the shield patterns 32B, 34B, and 36B located in the bent portions 13B and 13D is not particularly limited. For example, the planar shape of the through holes 32X, 34X, and 36X is not particularly limited as long as at least one corner is included. For example, the planar shape of the joint 45 is not particularly limited as long as at least one corner is included.

Figure 14:
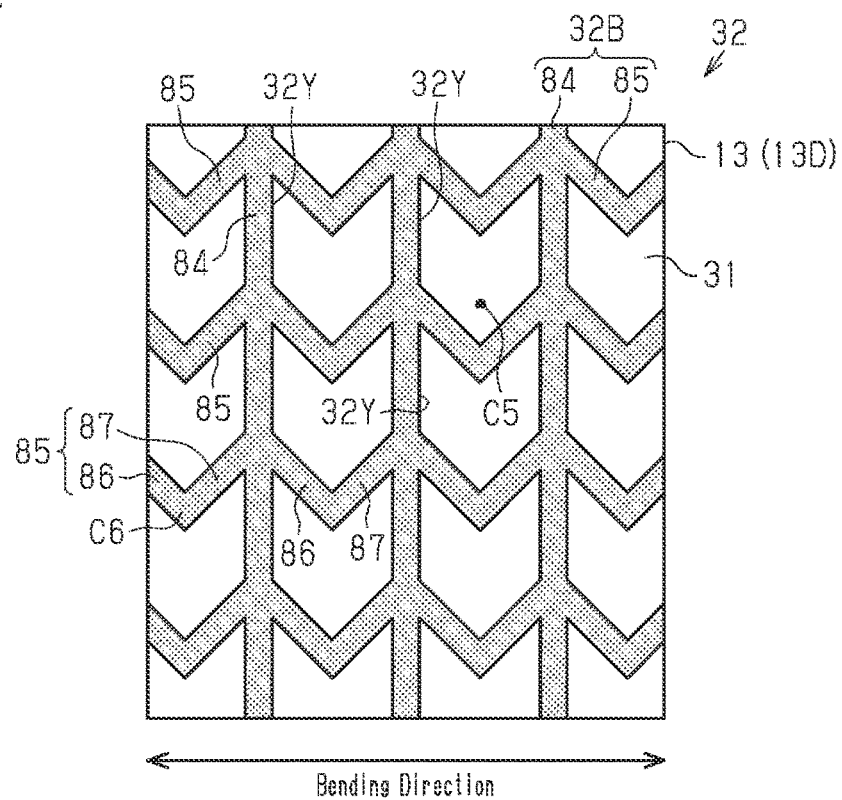
FIGS. 14 and 15 are schematic plan views illustrating various modified examples of a wiring substrate.

For example, as illustrated in FIG. 14, the shield pattern 32B located in the bent portion 13D may include V-shaped through holes 32Y having a planar shape including one corner C5. The through holes 32Y are arranged, for example, at given intervals in the bending direction and also at given intervals in a lateral direction that is orthogonal to the bending direction in plan view.

In the present example, the shield pattern 32B includes supports 84 extending parallel to each other in the lateral direction intersecting the bending direction in plan view and joints 85 formed between adjacent ones of the supports 84 and connecting the adjacent supports 84.

Each support 84 has, for example, a given width and extends straight. The supports 84 are, for example, arranged at given intervals in the bending direction. In the example illustrated in FIG. 14, three supports 84 are arranged. However, the number of supports 84 is not particularly limited. Two supports 84 may be arranged, or four or more supports 84 may be arranged.

The joints 85 are, for example, arranged at given intervals in the lateral direction, which is orthogonal to the bending direction, between adjacent ones of the supports 84. The joints 85 are, for example, arranged at given intervals in the bending direction. In the present example, the joints 85 that are arranged next to one another in the bending direction are located at the same position in the lateral direction. The joints 85 are, for example, the same in planar shape and size. The joints 85 are, for example, arranged in the same direction.

In the present example, the planar shape of each joint 85 is V-shaped and includes one corner C6. That is, the joint 85 includes an extension 86 and an extension 87. The extension 86 extends in a direction intersecting an extension direction of the support 84. The extension 87 extends from an end of the extension 86 in a direction intersecting the extension direction of the support 84 and an extension direction of the extension 86. In the present example, the extension 87 extends in a direction that intersects the extension direction of the support 84 and is orthogonal to the extension direction of the extension 86. That is, in each joint 85 of the present example, the extension 87 is substantially orthogonal to the extension 86. In the joint 85, the corner C6 is formed in the part that connects the extension 86 and the extension 87. For example, in the joint 85, the extension 86 and the extension 87 are located at the same position in the lateral direction. The extension 86 and the extension 87 are, for example, the same in planar shape and size. The extension 86 has an end connected to one of the adjacent supports 84. The extension 87 has an end connected to the other one of the adjacent supports 84. For example, the adjacent supports 84, the extension 86, and the extension 87 are formed continuously and integrally with each other.

As described above, in the shield pattern 32B of the present example, the planar shape of the joint 85 formed between the adjacent supports 84 includes one corner C6. As a result, the joint 85 has spring-like characteristics, and a favorable flexibility is obtained from the spring-like characteristics.

Although the details are not illustrated, the shield patterns 34B and 36B located in the bent portions 13B and 13D (refer to FIG. 4) include through holes having the same planar shape as the through holes 32Y and arranged at the same intervals as the through holes 32Y. For example, through holes formed in the shield patterns 32B, 34B, and 36B adjacent to each other in the stacking direction overlap in plan view.

In the embodiment, the planar shape of the joint 45 may include three or more corners. For example, the planar shape of the joints 45 may be W-shaped.

In the embodiment, the supports 44 of the shield pattern 32B extend in a direction orthogonal to the bending direction. However, there is no limitation to such a configuration.

Figure 15:
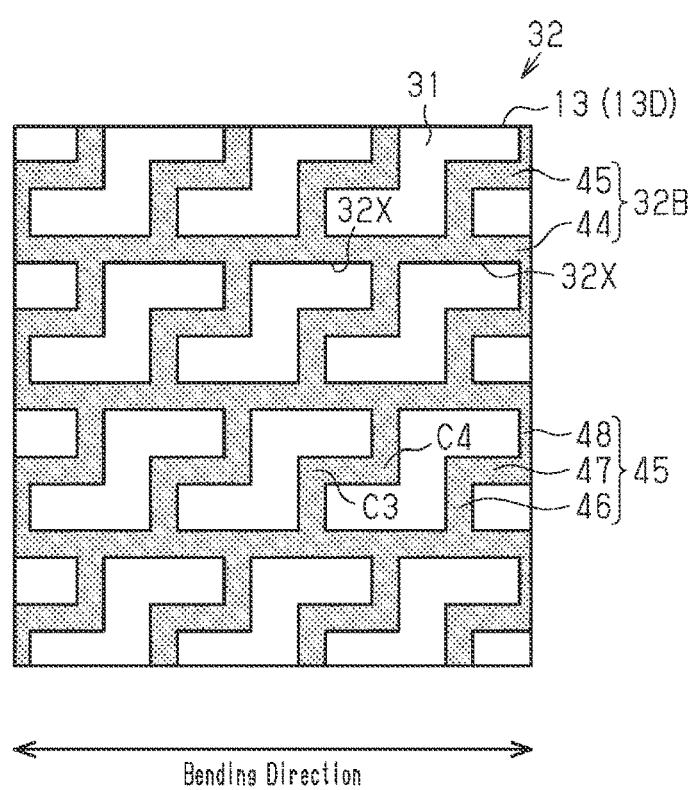

For example, as illustrated in FIG. 15, the supports 44 may extend in the bending direction. In this case, the joints 45 are formed between the supports 44 that are adjacent to each other in the lateral direction, which is orthogonal to the bending direction. The shield pattern 32B illustrated in FIG. 15 has a structure obtained when the shield pattern 32B illustrated in FIG. 5 is rotated ninety degrees to the right (clockwise) in plan view.

In the embodiment, the shield patterns 32B, 34B, and 36B located in the bent portion 13D have substantially the same planar shape. Instead, for example, the planar shape may differ between the shield patterns 32B, 34B, and 36B located in the bent portion 13D. For example, the planar shape of the joint 45 may differ between the shield patterns 32B, 34B, and 36B.

In the embodiment, the through holes 32X, 34X, and 36X having corners are formed in all of the shield patterns 32B, 34B, and 36B located in the bent portions 13B and 13D. Instead, the bent portions 13B and 13D may include a shield pattern that does not include a through hole including a corner. For example, in the shield patterns 32B, 34B, and 36B located in the bent portions 13B and 13D, the through holes 34X including corners may be formed in only the shield pattern 34B.

In the embodiment, the number of wiring layers in the wiring substrate 13 is not particularly limited. For example, the number of wiring layers in the bent portions 13B and 13D may be the same as the number of wiring layers in the mount portion 13C.

In the embodiment, the wiring substrate 13 is embodied in a coreless substrate. However, there is no limitation to such a configuration. For example, the wiring substrate 13 may be embodied in a wiring substrate having a core substrate.

All examples and conditional language recited herein are intended for pedagogical purposes to aid the reader in understanding the principles of the invention and the concepts contributed by the inventor to furthering the art, and are to be construed as being without limitation to such specifically recited examples and conditions, nor does the organization of such examples in the specification relate to an illustration of the superiority and inferiority of the invention. Although embodiments have been described in detail, it should be understood that various changes, substitutions, and alterations could be made hereto without departing from the scope of this disclosure.

What is claimed is:

1. An electronic device, comprising:
  a support body including
    a first planar portion and a second planar portion that are arranged facing each other,
    a first connecting portion connecting a first end of the first planar portion to a first end of the second planar portion, and
    a first receptacle surrounded by the first planar portion, the first connecting portion, and the second planar portion;
  a projection being part of the second planar portion, projecting outward from the first receptacle, and located outside the first planar portion in plan view;
  a wiring substrate including a facing surface facing the support body and an opposite surface so that the opposite surface and the facing surface are located at opposite sides of the wiring substrate, the wiring substrate being folded and attached along an inner surface of the first receptacle and also being attached along a first surface of the projection that is continuous with the inner surface of the first receptacle;
  a sensor element mounted on the facing surface of the wiring substrate at a portion of the wiring substrate attached to the inner surface of the first receptacle; and
  an antenna mounted on the opposite surface of the wiring substrate at a portion of the wiring substrate attached to the first surface of the projection.

2. The electronic device according to claim 1, wherein
  an inner surface of the first receptacle includes a first surface of the first planar portion,
  an outer surface of the first receptacle include a second surface of the first planar portion located at a side opposite to the first surface of the first planar portion,
  the wiring substrate is attached along the first surface of the first planar portion, folded on the second surface of the first planar portion at a second end of the first planar portion, and attached along the second surface of the first planar portion, and
  the electronic device further comprises a battery module mounted on the opposite surface of the wiring substrate at a portion of the wiring substrate attached to the second surface of the first planar portion.

3. The electronic device according to claim 1, wherein
  an inner surface of the first receptacle includes a first end surface of the first connecting portion along which the wiring substrate is attached, the wiring substrate includes a bent portion that is bent at the first end surface of the first connecting portion, the wiring substrate has a structure in which wiring layers and insulation layers are alternately stacked, at least one of the wiring layers includes a shield pattern, the shield pattern located in the bent portion includes through holes arranged at a given interval, and each of the through holes has a planar shape including at least one corner.

4. The electronic device according to claim 3, wherein the shield pattern located in the bent portion includes supports extending parallel to each other in a direction orthogonal to a bending direction of the bent portion, and a joint arranged between adjacent ones of the supports and connecting the adjacent ones of the supports, wherein the joint has a crank-shaped planar shape including two corners.

5. The electronic device according to claim 1, wherein the support body further includes a second receptacle, a third planar portion arranged facing the second planar portion and including a first end as a free end and a second end so that the free end and the second end are located at opposite sides of the third planar portion, a second connecting portion connecting a second end of the second planar portion to the second end of the third planar portion, the second end of the second planar portion including the projection, and a second receptacle surrounded by the second planar portion, the third planar portion, and the second connecting portion and configured to receive a measurement subject.

6. The electronic device according to claim 5, wherein a distance in the projection between an inner surface of the second receptacle and an outer surface of the second receptacle is greater than a distance in the second planar portion excluding the projection between the inner surface of the second receptacle and the outer surface of the second receptacle.

7. The electronic device according to claim 6, wherein the outer surface of the second receptacle includes a first end surface of the second connecting portion, the first end surface of the second connecting portion being flat in a first direction in which the second planar portion and the third planar portion are arranged facing each other, the inner surface of the second receptacle includes a second end surface of the second connecting portion, the second end surface of the second connecting portion being located at a side opposite to the first end surface, and the second end surface of the second connecting portion being curved and recessed toward an inner side of the second connecting portion, and a recess amount of the second end surface of the second connecting portion is increased from each of the second planar portion and the third planar portion toward a center of the second connecting portion in the first direction.

8. The electronic device according to claim 5, wherein the sensor element includes a first sensor element, an outer surface of the second receptacle includes a first surface of the third planar portion, the wiring substrate includes a mount portion covering the first surface of the third planar portion, and the electronic device further comprises a second sensor element mounted on the mount portion and facing the first sensor element.

9. The electronic device according to claim 8, wherein the second planar portion includes a first through hole extending though the second planar portion in a position that overlaps the first sensor element in plan view, and the third planar portion includes a second through hole extending through the third planar portion in a position that overlaps the second sensor element in plan view.

10. The electronic device according to claim 9, wherein the first sensor element is accommodated in the first through hole, and the second sensor element is accommodated in the second through hole.

* * * * *